United States Patent
Nam et al.

(10) Patent No.: US 9,493,423 B2
(45) Date of Patent: Nov. 15, 2016

(54) COMPOUNDS CAPABLE OF INHIBITING VOLTAGE GATED CALCIUM ION CHANNEL, AND PHARMACEUTICAL COMPOSITIONS COMPRISING THE SAME

(71) Applicant: KOREA INSTITUTE OF SCIENCE AND TECHNOLOGY, Seoul (KR)

(72) Inventors: Ghil Soo Nam, Seoul (KR); Kyung Il Choi, Seoul (KR); Jung Hyun Kim, Seoul (KR); Ae Nim Pae, Seoul (KR); Jin Ri Hong, Bucheon-si (KR); Jae Kyun Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/632,839

(22) Filed: Feb. 26, 2015

(65) Prior Publication Data

US 2015/0329533 A1    Nov. 19, 2015

(51) Int. Cl.
  *C07D 231/12*    (2006.01)
  *C07D 417/14*    (2006.01)
  *C07D 401/12*    (2006.01)
  *C07D 417/06*    (2006.01)

(52) U.S. Cl.
  CPC .......... *C07D 231/12* (2013.01); *C07D 401/12* (2013.01); *C07D 417/06* (2013.01); *C07D 417/14* (2013.01)

(58) Field of Classification Search
  CPC  C07D 231/12; C07D 417/06; C07D 417/14; C07D 401/12
  See application file for complete search history.

(56) References Cited

U.S. PATENT DOCUMENTS

| | | | |
|---|---|---|---|
| 7,297,710 B1 | 11/2007 | Barth et al. | |
| 7,875,646 B2 | 1/2011 | Barth et al. | |
| 8,703,749 B2* | 4/2014 | Testi | A61K 31/63 514/155 |
| 9,090,566 B2* | 7/2015 | Carling | C07D 231/14 |
| 2013/0310377 A1 | 11/2013 | Muthuppalaniappan et al. | |

FOREIGN PATENT DOCUMENTS

| | | |
|---|---|---|
| KR | 1020060105050 A | 9/2016 |
| WO | WO 98/49149 A1 | 11/1998 |
| WO | WO 2005/073197 A1 | 11/2005 |

OTHER PUBLICATIONS

Mason, J Am Collee of Cardiology, vol. 34(7), 1857-1866, 1999.*
Khosravani Houman et al., "Effects of Cav3.2 channel mutations linked to idiopathic generalized epilepsy", Annals of Neurology, 2005, pp. 745-749,vol. 57 (5),Wiley-Liss, Inc., through Wiley Subscription Services, USA.
Iuliia Vitko et al., "Functional Characterization and Neuronal Modeling of the Effects of Childhood Absence Epilepsy Variants of CACNA1H, a T-Type Calcium Channel", Journal of Neuroscience, May 11, 2005, pp. 4844-4855, vol. 25 (19), China.
Jean-Paulclozel et al.,The Structurally Novel Ca 2 + Channel Blocker Ro 40-5967, Which Binds to the [3H] Desmethoxyverapamil Receptor, is Devoid of the Negative Inotropic Effects of Verapamil in Normal and Failing Rat HeartsCardiovascular Drugs and Therapy ,1990,pp. 731-736,vol. 4,Kluwer Academic Publishers,U.S.A.
Hefti et al., Antihypertensive Properties of the Novel Calcium Antagonist(1S,2S-2-[2-[[3-(2-Benzimidazolyl)propyl]methylamino]ethyl]-6-fluoro-1,2,3,4-terahydro-1-isopropyl-2-naphthylMethoxyacetate Dihydrochloride in Rat Models o Hypertension, Arzneimittel for schung ,1990,pp. 417-421,vol. 40, Switzerland.
Sven Moosmang et al., Antihypertensive Effects of the Putative T-Type CalciumChannel Antagonist Mibefradil are Mediated by the L-TypeCalcium Channel Cav1.2 , Circulation Research ,2006,pp. 105-110, vol. 98 (1), German.
Giorgio Santoni et al., Functional role of T-type calcium channels in tumour growth and progression: prospective in cancer therapy,British Journal of Pharmacology ,2012,pp. 1244-1246 ,vol. 166,The Authors, British.
Ahmet Dogrul et al. Reversal of experimental neuropathic pain by T-type calcium channel blockers,Pain ,2003,pp. 159-168,vol. 105, International Association for the Study of Pain/ Elsevier B.V.

* cited by examiner

*Primary Examiner* — D M Seaman
(74) *Attorney, Agent, or Firm* — Goldilocks Zone IP Law

(57) ABSTRACT

Disclosed herein are an N-(pyrazolylmethyl)arylsulfonamide derivative useful as a calcium ion channel blocker, a pharmaceutically acceptable salt thereof, and the medicinal use thereof as a therapeutic agent using its calcium ion channel blocking effect.

12 Claims, 2 Drawing Sheets

COMPOUNDS CAPABLE OF INHIBITING VOLTAGE GATED CALCIUM ION CHANNEL, AND PHARMACEUTICAL COMPOSITIONS COMPRISING THE SAME

CROSS-REFERENCE TO RELATED APPLICATION

This application claims under 35 U.S.C. §119(a) the benefit of Korean Patent Application No. 10-2014-0058621 filed on May 15, 2014, the entire contents of which are incorporated herein by reference.

BACKGROUND

1. Technical Field

The present invention relates to N-(pyrazolylmethyl)arylsulfonamide derivatives useful as calcium ion channel blockers, pharmaceutically acceptable salts thereof, and the medicinal use thereof as therapeutic agents using their calcium ion channel blocking effect.

2. Background Art

Voltage-gated calcium ion channels play an important role in intracellular signal transmission by increasing calcium inflow to cells in response to neural stimuli. These calcium channels are classified as high-voltage activated calcium channels and low-voltage activated calcium channels. Representative among low-voltage activated calcium channels are T-type calcium channels.

T-type calcium ion channels are found in central muscles, endocrine glands in the adrenal, sinoatrial node, heart, etc. T-type calcium channel antagonists are known to exert therapeutic effects on cerebral and cardiac diseases such as epilepsy, hypertension, angina pectoris, etc. [1] Hosravani, Houman et al., "Effects of Cav3.2 channel mutations linked to idiopathic generalized epilepsy", Annals of Neurology (2005), 57 (5), 745-749; 2) Vitko, Iuliia et al., "Functional characterization and neuronal modeling of the effects of childhood absence epilepsy variants of CACNA1H, a T-type calcium channel", Journal of Neuroscience (2005), 25 (19), 4844-4855; 3) Clozel, Cardiovas Drugs Ther. (1990), 4, pp. 731-736; 4) Hefti, Arzneimittelforschung (1990), 40, 417-421; 5) Moosmang, Sven et al., "Antihypertensive Effects of the Putative T-Type Calcium Channel Antagonist Mibefradil Are Mediated by the L-Type Calcium Channel Cav1. 2", Circulation Research (2006), 98 (1), 105-110].

T-type calcium channels are also involved in cancer cell growth, and T-type calcium channel blockers are reported to be useful as anti-cancer agents inhibiting cancer cell growth ["Functional role of T-type calcium channel in tumor growth and progression: prospective in cancer therapy" British Journal of Pharmacology, (2012), 166, 1244-1246].

In addition, recent reports have disclosed therapeutic effects of T-type calcium ion channel blockers on pain. Briefly, Mibefradil and Ethosuximide, both known as T-type calcium ion channel antagonists, were reported to reverse mechanical and thermal pain induction dose-dependently in a spinal nerve ligation animal model, demonstrating that the T-type calcium ion channel antagonists have a therapeutic effect on neuropathic pain [Dogrul, Ahmet et al., "Reversal of experimental neuropathic pain by T-type calcium channel blockers", Pain, 2003, 105, 159-168].

Mibefradil, developed as a T-type calcium ion channel antagonist (Mibefradil, Ro 40-5967, WO 98/49149), was used to treat hypertension and angina pectoris, but was withdrawn from the market due to the unfavorable drug-drug interaction caused by cytochromes P-450 3A4 and 2D6. Substantially no drugs are available as T-type calcium ion channel blockers, and therefore the need for the development of a novel T-type calcium ion channel blocker is urgent.

WO 2005/073197 discloses derivatives of N'-(1,5-diphenyl-1H-pyrazol-3-yl)sulfonamide, represented by the following Chemical Formula A:

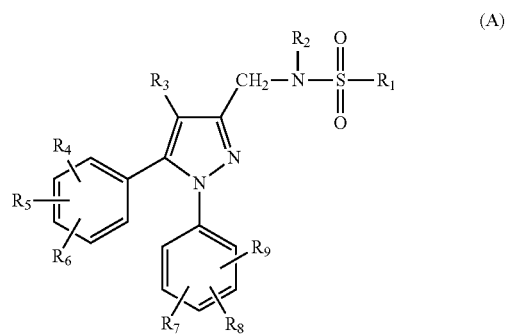

(A)

In this patent document, the compound of Chemical Formula A is demonstrated to have antagonistic activity against the cannabinoid receptor type 1 (CB1), and described to be useful for the treatment of appetite disorders, gastric disorders, inflammations, immune system diseases, psychotic disorders, alcohol dependence, and nicotine dependence.

Leading to the present invention, intensive and thorough research into the development of novel compounds acting on calcium ion channels was carried out, and was found that novel N-(pyrazolylmethyl)arylsulfonamide derivatives exhibit excellent antagonistic activity against T-type calcium ion channels. The novel compounds of the present invention, which have a substituted or unsubstituted phenyl group at either N1 or C5 position of the pyrazole ring moiety, and an alkyl group at the position, not occupied by the phenyl group, exhibit excellent antagonistic activity against T-type calcium ion channels.

SUMMARY

It is an object of the present invention to provide novel N-(pyrazolylmethyl)arylsulfonamide derivatives with a variety of substituents, and pharmaceutically acceptable salts thereof.

It is another object of the present invention to provide pharmaceutical compositions for the treatment and prevention of cerebral diseases, cardiac diseases, cancerous diseases, or pain syndromes, the composition comprising the N-(pyrazolylmethyl)arylsulfonamide derivative or a pharmaceutically acceptable salt thereof as an active ingredient functioning to effectively block T-type calcium ion channels.

To accomplish the above objects, the present invention provides N-(pyrazolylmethyl)arylsulfonamide derivatives, represented by the following Chemical Formula 1, having selective antagonistic activity against T-type calcium ion channels, and pharmaceutically acceptable salts thereof.

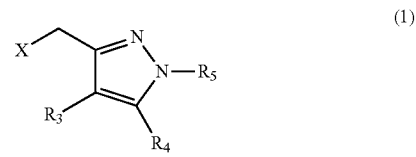

(1)

wherein,
X is

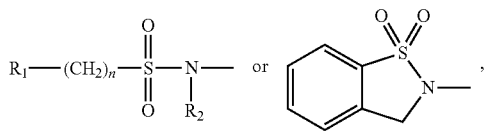 or 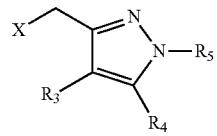

Wherein,
$R_1$ represents $C_6\sim C_{12}$ aryl unsubstituted or substituted by one to three substituents selected from the group consisting of halo, $C_1\sim C_6$ alkyl and piperidin-1-yl, or 5- to 12-membered heteroaryl with 1 to 3 nitrogen atoms,
$R_2$ represents a hydrogen atom, or $C_1\sim C_6$ alkyl,
$R_3$ represents a hydrogen atom, or $C_1\sim C_6$ alkyl,
$R_4$ and $R_5$ independently represent $C_1\sim C_6$ alkyl, or phenyl unsubstituted or substituted by a substituent selected from the group consisting of halo, $C_1\sim C_6$ alkyl, $C_1\sim C_6$ haloalkyl, and piperidin-1-yl, with the proviso that any one of $R_4$ and $R_5$ is substituted or unsubstituted phenyl while the other represents $C_1\sim C_6$ alkyl, and
n is an integer of 0 to 6.

The novel compounds of the present invention exhibit effective activity as T-type calcium ion channel blockers.

Having an antagonistic activity against T-type calcium ion channels, the novel compounds of the present invention can be pharmaceutically effective for the therapy and prophylaxis of cerebral diseases, cardiac diseases, cancers, or pain diseases induced by the activity of T-type calcium ion channels. In detail, the novel compounds of the present invention are useful as therapeutic or preventative agents of cerebral diseases such as epilepsy, depression, dementia, sleep disorder, diabetes, obesity, etc.; heart diseases such as hypertensive, cardiac arrhythmia, angina pectoris, myocardial infarction, and congestive heart failure; cancers such as hepatic cancer, lung cancer, rectal cancer, prostate cancer, breast cancer, uterine cancer, esophageal cancer, brain cancer, etc.; pain syndrome such as chronic and acute pain, neuropathic pain, etc.

BRIEF DESCRIPTION OF THE DRAWINGS

The above and other objects, features and other advantages of the present invention will be more clearly understood from the following detailed description taken in conjunction with the accompanying drawings, in which
In FIGS. 1 and 2, PWT (paw withdrawal threshold; A and C), and % MPE (maximum possible effect; B and D) are analyzed.
*P<0.05 (gabapentin), *P<0.05 (compounds of the present invention) vs. pre-administration value (paired t-test)
♣ P<0.05 gabapentin vs. compounds of the present invention (unpaired t-test)

DETAILED DESCRIPTION

Figure 1:
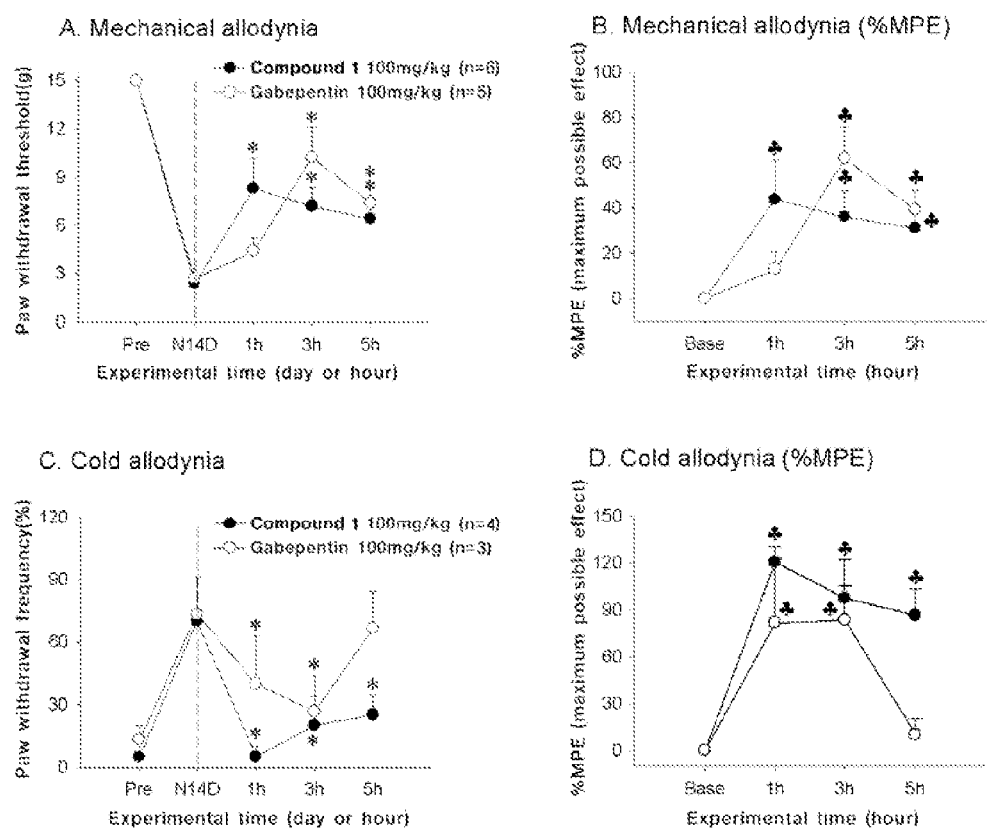
FIG. 1 shows therapeutic effect of the compound 1 according to the present invention on mechanical allodynia and cold allodynia, in comparison with gabapentin.

In accordance with an aspect thereof, the present invention addresses N-(pyrazolylmethyl)arylsulfonamide derivatives represented by the following Chemical Formula 1:

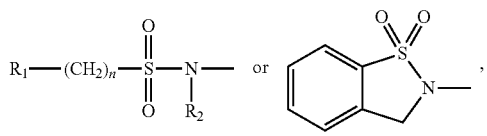

wherein,
X is

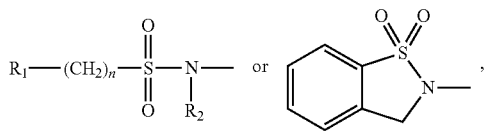 or 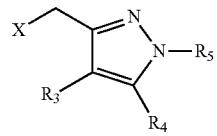

Wherein,
$R_1$ represents $C_6\sim C_{12}$ aryl unsubstituted or substituted by one to three substituents selected from the group consisting of halo, $C_1\sim C_6$ alkyl and piperidin-1-yl, or 5- to 12-membered heteroaryl with 1 to 3 nitrogen atoms,
$R_2$ represents a hydrogen atom, or $C_1\sim C_6$ alkyl,
$R_3$ represents a hydrogen atom, or $C_1\sim C_6$ alkyl,
$R_4$ and $R_5$ independently represent $C_1\sim C_6$ alkyl, or phenyl unsubstituted or substituted by a substituent selected from the group consisting of halo, $C_1\sim C_6$ alkyl, $C_1\sim C_6$ haloalkyl, and piperidin-1-yl, with the proviso that any one of $R_4$ and $R_5$ is substituted or unsubstituted phenyl while the other represents $C_1\sim C_6$ alkyl, and
n is an integer of 0 to 6.

In addition, the N-(pyrazolylmethyl)arylsulfonamide derivatives, represented by Chemical Formula 1, according to the present invention may contain a chiral center, and may exist as racemates or individual optical isomers, all of which fall within the scope of the present invention.

Further, the present invention includes radioactive version of the N-(pyrazolylmethyl)arylsulfonamide derivatives represented by Chemical Formula 1, and the radioactive version is useful in the diagnosis field.

Meanwhile, the N-(pyrazolylmethyl)arylsulfonamide derivatives, represented by Chemical Formula 1, according to the present invention may form pharmaceutically acceptable salts using methods typical of the art. For example, innoxious inorganic acids, such as hydrochloric acid, bromic acid, sulfonic acid, amidosulfonic acid, phosphoric acid, and nitric acid, or innoxious organic acids, such as propionic acid, succinic acid, glycolic acid, stearic acid, lactic acid, tartaric acid, citric acid, p-toluenesulfonic acid, methanesulfonic acid, etc., may be used to form pharmaceutically acceptable salts of the novel derivatives.

Detailed explanation of substituents on the N-(pyrazolylmethyl)arylsulfonamide derivatives represented by Chemical Formula 1 is given below. The term 'alkyl' is intended to encompass straight, branched, or cyclic carbon chains of 1 to 6 carbon atoms, with preference for methyl, ethyl, propyl, isopropyl, butyl, isobutyl, tert-butyl, neopentyl, cyclopentyl, and cyclohexyl. The term 'haloalkyl' is intended to encompass straight, branched, or cyclic alkyl having 1 to 10 halogen atoms as substituents, with preference for chloromethyl, 1,2-dichloroethyl, and trifluoromethyl. In the context of organic molecules, 'aryl' refers to any functional group or substituent derived from an aromatic ring. Aryl encompasses a stable state by resonance of electrons in double bonds between adjacent carbon atoms such as in one aromatic ring containing at least 6 atoms, or two aromatic rings containing at least 10 atoms. Examples of aryl include phenyl, biphenyl, and naphthyl. Aryl may have one or more substituents selected from among halogen atoms and alkyl. The term 'benzyl' refers to a functional group possessing aryl substituted with methylene that can form a covalent bond with a different atom. The term 'heteroaryl' refers to a 5- to 12-membered, stable heterocyclic compound, whether single ring or fused ring, having a nitrogen atom as a member. Examples of heteroaryl include pyrrole, imidazole, pyrazole, triazole, pyridine, pyrimidine, pyridazine, triazine, indazole, benzimidazole, quinoline, isoquinoline, quinazole, quinoxaline, and phthalazine. The heteroaryl may be substituted with at least one substituent selected from among halogen atoms, and alkyl radicals.

The N-(pyrazolylmethyl)arylsulfonamide of the present invention may be represented by the following Chemical Formula 1a or 1b according to the substituent X:

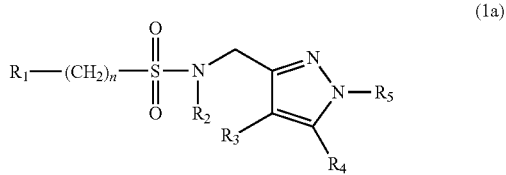

(1a)

(wherein $R_1$, $R_2$, $R_3$, $R_4$, $R_5$, and n are respectively as defined above)

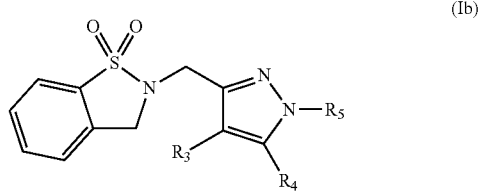

(1b)

(wherein $R_3$, $R_4$, and $R_5$ are respectively as defined above)

In a preferred embodiment of the compound represented by Chemical Formula 1a, $R_1$ represents phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-methylphenyl, 4-tert-butylphenyl, 2-fluoro-5-methylphenyl, 2-methyl-3-chlorophenyl, 4-cyclohexylphenyl, 4-(piperidin-1-yl)phenyl, naphthalen-1-yl, naphthalen-2-yl, or quinolin-8-yl; $R_2$ and $R_3$, which may be the same or different, represent a hydrogen atom, methyl, or ethyl; when $R_4$ is methyl, ethyl, propyl, isopropyl, butyl, isobutyl, or tert-butyl, $R_5$ represents phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl; when $R_4$ is phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl, $R_5$ represents methyl, ethyl, propyl, isopropyl, butyl, isobutyl, or tert-butyl.

In a preferred embodiment of the compound represented by Chemical Formula 1b, $R_3$ represents a hydrogen atom, methyl, or ethyl; when $R_4$ is methyl, ethyl, propyl, isopropyl, butyl, isobutyl, or tert-butyl, $R_5$ represents phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl; when $R_5$ is phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl, $R_5$ represents methyl, ethyl, propyl, isopropyl, butyl, isobutyl, or tert-butyl.

Concrete examples of the N-(pyrazolylmethyl)arylsulfonamide derivatives, represented by Chemical Formula 1, according to the present invention include:

Compound 1. N-[(5-isobutyl-1-phenyl-1H-pyrazol-3-yl)methyl]benzenesulfonamide;
Compound 2. N-[(5-isobutyl-1-phenyl-1H-pyrazol-3-yl)methyl]-3-fluorobenzenesulfonamide;
Compound 3. N-[(5-isobutyl-1-phenyl-1H-pyrazol-3-yl)methyl]-3-chlorobenzenesulfonamide;
Compound 4. N-[(5-isobutyl-1-phenyl-1H-pyrazol-3-yl)methyl]-4-methylbenzenesulfonamide;
Compound 5. N-[(5-isobutyl-1-phenyl-1H-pyrazol-3-yl)methyl]-4-iodobenzenesulfonamide;
Compound 6. N-[(5-isobutyl-1-phenyl-1H-pyrazol-3-yl)methyl]-4-tert-butylbenzenesulfonamide;
Compound 7. N-[(5-isobutyl-1-phenyl-1H-pyrazol-3-yl)methyl]benzylsulfonamide;
Compound 8. N-[(5-isobutyl-1-phenyl-1H-pyrazol-3-yl)methyl]naphthalene-1-sulfonamide;
Compound 9. N-[(5-isobutyl-1-phenyl-1H-pyrazol-3-yl)methyl]naphthalene-2-sulfonamide;
Compound 10. N-[(5-isobutyl-1-phenyl-1H-pyrazol-3-yl)methyl]quinoline-8-sulfonamide;
Compound 11. N-[(5-isobutyl-1-phenyl-1H-pyrazol-3-yl)methyl]-(2-fluoro-5-methyl)benzenesulfonamide;
Compound 12. N-[(5-isobutyl-1-phenyl-1H-pyrazol-3-yl)methyl]-(2-methyl-3-chloro)benzenesulfonamide;
Compound 13. N-[(5-isobutyl-1-phenyl-1H-pyrazol-3-yl)methyl]-2,6-difluorobenzenesulfonamide;
Compound 14. N-[(5-isobutyl-1-phenyl-1H-pyrazol-3-yl)methyl]-2,6-dichlorobenzenesulfonamide;
Compound 15. N-[(5-isobutyl-4-methyl-1-phenyl-1H-pyrazol-3-yl)methyl]benzenesulfonamide;
Compound 16. N-[(5-isobutyl-4-methyl-1-phenyl-1H-pyrazol-3-yl)methyl]naphthalene-2-sulfonamide;
Compound 17. N-[(5-isobutyl-4-ethyl-1-phenyl-1H-pyrazol-3-yl)methyl]benzenesulfonamide;
Compound 18. N-methyl-N-[(5-isobutyl-1-phenyl-1H-pyrazol-3-yl)methyl]benzenesulfonamide;
Compound 19. N-[(5-isobutyl-1-phenyl-1H-pyrazol-3-yl)methyl]-2-phenylethanesulfonamide;
Compound 20. N-[(5-isobutyl-1-(4-fluorophenyl)-1H-pyrazol-3-yl)methyl]benzenesulfonamide;
Compound 21. N-[{1-(4-fluorophenyl)-5-isobutyl-1H-pyrazol-3-yl}methyl]quinoline-8-sulfonamide;
Compound 22. N-[{1-(tert-butyl)-5-(4-fluorophenyl)-1H-pyrazol-3-yl}methyl]benzenesulfonamide;
Compound 23. N-[{1-(tert-butyl)-5-phenyl-1H-pyrazol-3-yl}methyl]benzenesulfonamide;
Compound 24. N-(5-isobutyl-1-phenyl-1H-pyrazol-3-yl)-1-(naphthalen-2-yl)methanesulfonamide;
Compound 25. N-{1-(4-fluorophenyl)-5-isobutyl-1H-pyrazol-3-yl}-1-(naphthalen-2-yl)methanesulfonamide;
Compound 26. N-{[1-(tert-butyl)-5-{4-(piperidin-1-yl)phenyl-1H-pyrazol-3-yl]methyl}benzenesulfonamide;
Compound 27. N-{[1-(tert-butyl)-5-(4-cyclohexylphenyl)-1H-pyrazol-3-yl]methyl}benzenesulfonamide;

Compound 28. 2-((5-isobutyl-1-phenyl-1H-pyrazol-3-yl)methyl)-2,3-dihydrobenzo[d]iso(xa)thiazole-1,1-dioxide;

Compound 29. 2-[{1-(tert-butyl)-5-isobutyl-1H-pyrazol-3-yl}methyl]-2,3-dihydro[d]isothiazole 1,1-dioxide;

Compound 30. 2-[{1-(4-fluorophenyl)-5-isobutyl-1H-pyrazol-3-yl}methyl]-2,3-dihydro[d]isothiazole 1,1-dioxide;

Compound 31. 2-[{1-(2,6-dichlorophenyl)-5-isobutyl-1H-pyrazol-3-yl}methyl]-2,3-dihydro[d]isothiazole 1,1-dioxide;

Compound 32. 2-[{1-(tert-butyl)-5-phenyl-1H-pyrazol-3-yl}methyl]-2,3-dihydro[d]isothiazole 1,1-dioxide;

Compound 33. 2-[{1-(tert-butyl)-5-(4-fluorophenyl)-1H-pyrazol-3-yl}methyl]-2,3-dihydro[d]isothiazole 1,1-dioxide;

Compound 34. 2-[{1-(tert-butyl)-5-(4-trifluoromethylphenyl)-1H-pyrazol-3-yl}methyl]-2,3-dihydro[d]isothiazole 1,1-dioxide;

Compound 35. 2-[{1-(tert-butyl)-5-(4-piperidin-1-yl-phenyl)-1H-pyrazol-3-yl}methyl]-2,3-dihydro[d]isothiazole 1,1-dioxide;

Compound 36. 2-[{1-(tert-butyl)-5-(4-cyclohexylphenyl)-1H-pyrazol-3-yl}methyl]-2,3-dihydro[d]isothiazole 1,1-dioxide;

Compound 37. 2-{(1-isobutyl-5-phenyl-1H-pyrazol-3-yl)methyl}-2,3-dihydro[d]isothiazole 1,1-dioxide; and Compound 38. 2-[{5-(4-fluorophenyl)-1-isobutyl-1H-pyrazol-3-yl}methyl]-2,3-dihydro[d]isothiazole 1,1-dioxide.

Contemplated in accordance with another aspect of the present invention is a method for preparing an N-(pyrazolylmethyl)arylsulfonamide derivatives represented by Chemical Formula 1.

A method for preparing the compound of Chemical Formula 1a in accordance with an embodiment of the present invention can be carried out as representatively illustrated in the following Reaction Scheme 1. According to the preparation method of the Reaction Scheme 1, a pyrazolylmethylamine compound of Chemical Formula 2 is subjected to a nucleophilic substitution reaction with a sulfonyl halide compound of Chemical Formula 3, followed by alkylating the nucleophilic substitution product with an alkyl halide, represented by R$_2$—X, to prepare N-(pyrazolylmethyl)arylsulfonamide derivatives, represented by Chemical Formula 1, in which various substituents R$_2$ are introduced.

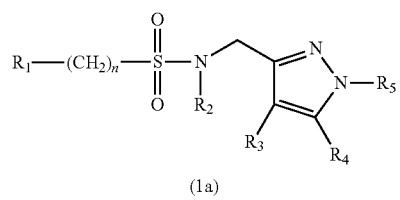

(1a)

(wherein R$_1$, R$_2$, R$_3$, R$_4$, R$_5$, and n are respectively as defined above).

In Scheme 1, the nucleophilic substitution reaction and the alkylation may be carried out with typical processes using suitable bases and organic solvents known in the art. Within the scope of the bases useful in the reactions, inorganic salts such as carbonates, sulfates and hydroxides of alkali metals or alkaline earth metals, or organic bases such as mono(C$_1$-C$_5$ alkyl)amine and di(C$_1$-C$_5$ alkyl)amine may fall. The solvents may be inert organic solvents typically used in the art, without influence on the reactions. Concrete examples of the organic solvents available in the present invention include lower alcohols of 1 to 6 carbon atoms such as methanol, ethanol, propanol, etc.; ethers such as diethyl ether, tetrahydrofuran, etc.; halogenated hydrocarbons such as chloroform, methylene chloride, etc.; nitriles such as acetonitrile, etc.; and amides such as N,N-dimethylformamide, N,N-dimethylacetamide, etc. The reactions of Scheme 1 may be conducted at 0° C. to the reflux temperature of the used solvent. In more detail, the reaction temperature may range from room temperature to 100° C., and preferably from 30° C. to 60° C.

As a starting material in Scheme 1, the pyrazolylmethylamine compound represented by Chemical Formula 2 may be prepared using the method illustrated in the following Reaction Scheme 2.

[Scheme 1]

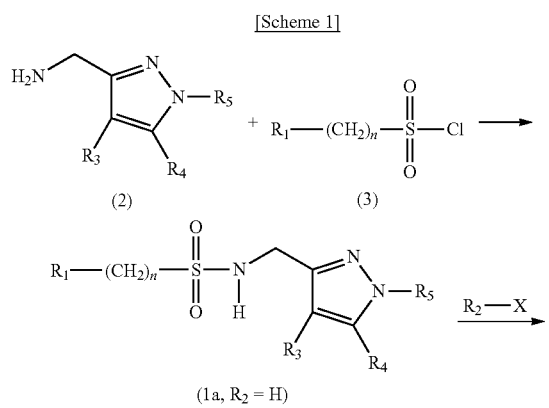

[Scheme 2]

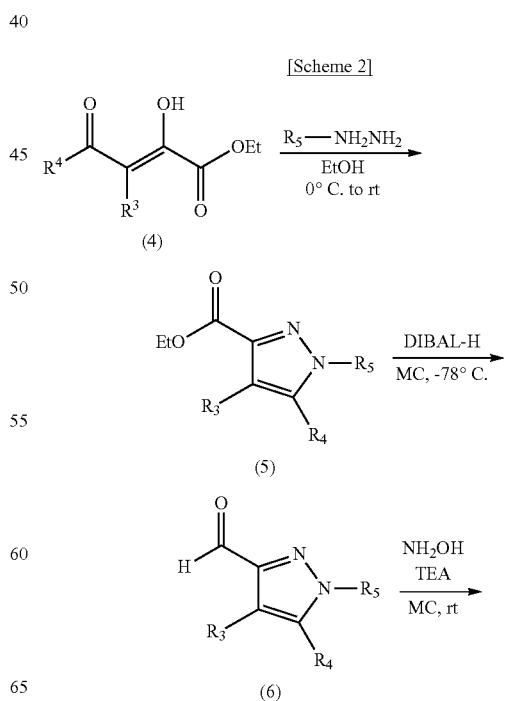

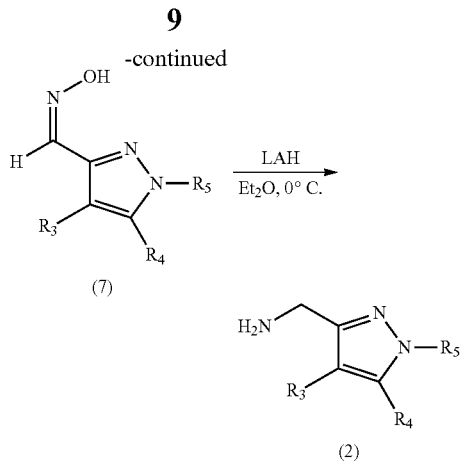

(wherein $R_3$, $R_4$, and $R_5$ are respectively as defined above)

As can be seen in Reaction Scheme 2, the preparation method comprises: reacting an ester compound of Chemical Formula 4 with an $R_5$-substituted hydrazine compound to form a pyrazol-3-yl carboxylate compound of Chemical Formula 5; reducing the pyrazol-3-ylcarboxylate compound of Chemical Formula 5 into a pyrazol-3-ylaldehyde of Chemical Formula 6; condensing the pyrazol-3-ylaldehyde compound of Chemical Formula 6 with hydroxylamine ($NH_2OH$) to synthesize a pyrazole-3-oxime compound of Chemical Formula 7; reducing the pyrazole-3-oxime compound of Chemical Formula 7 in the presence of lithium aluminum hydride (LAH) to afford the pyrazolylmethylamine compound of Chemical Formula 2.

In addition, the compound of Chemical Formula 1b may be prepared using a method illustrated in the following Reaction Scheme 3. As can be seen in Reaction Scheme 3, the N-(pyrazolylmethyl)arylsulfonamide derivative of Chemical-Formula 1b is prepared by subjecting a 1,2-benzisothiazoline-1,1-dioxide compound of Chemical Formula 8 to a substitution reaction with a pyrazolylmethyl halide compound of Chemical Formula 9 in the presence of a base.

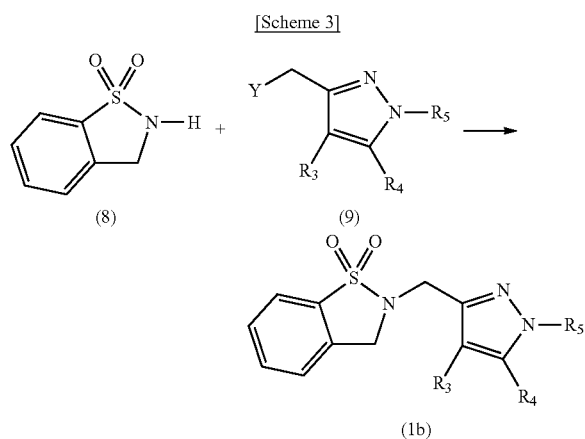

(wherein $R_3$, $R_4$, and $R_5$ are respectively as defined above, and Y is a leaving group selected from among a halogen atom, tosylate, and mesylate)

The substitution reaction in Reaction Scheme 3 may be carried out in a typical process using the same bases and organic solvents as in the nucleophilic substitution reaction and alkylation of Reaction Scheme 1. In the Example section described later, for the most part, potassium carbonate is used as a base while the solvent is selected from among methylene chloride and N,N-dimethylformamide, but it should be understood that other bases and solvents can be employed. As for the reaction temperature for the substitution reaction, its range may be from 0° C. to the reflux temperature of the solvent used, and more preferably from 20° C. to 40° C.

As starting materials in Reaction Scheme 3, 1,2-benzisothiazoline-1,1-dioxide of Chemical Formula 8, and pyrazolylmethyl halide of Chemical Formula 9 are well known in the art, and may be readily synthesized using typical methods as illustrated in Reaction Schemes 4 and 5, respectively.

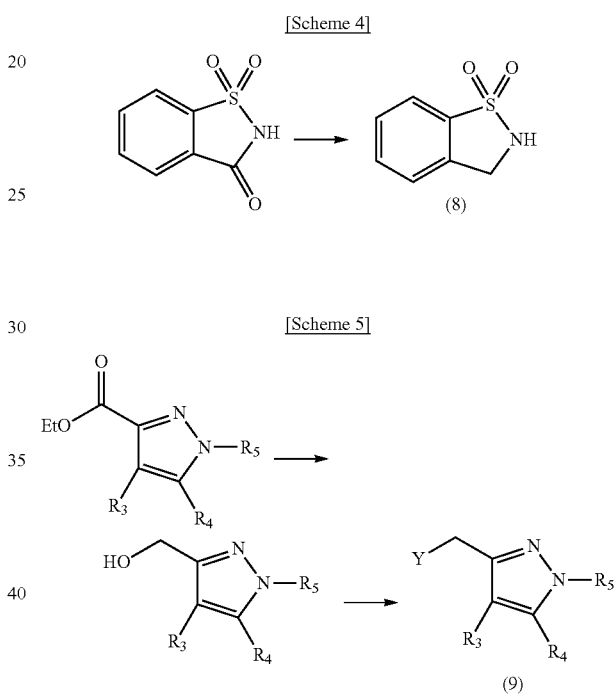

(wherein Y represents a leaving group selected from among a halogen atom, tosylate, and mesylate).

Further, pharmaceutically acceptable salts of the compound represented by Chemical Formula 1 can be readily prepared using a typical method disclosed in documents, and can be isolated as pure forms without any purification processes. Below, explanation is made of a preparation method of pharmaceutically acceptable salts of the compound represented by Chemical Formula 1, with a focus imposed on hydrochloride. The N-(pyrazolylmethyl)arylsulfonamide derivative represented by Chemical Formula 1 was dissolved in dichloromethane, and then 1 to 10 equivalents of a hydrogen chloride solution was added to give a hydrochloride of the target compound as solid. An organic solvent available for preparing a hydrogen chloride solution may be selected from among chloroform, dichloromethane, diethyl ether, methanol, ethyl acetate or a mixture thereof, with diethyl ether being preferred. The product in a solid state may be isolated by centrifugation or by a simple solvent remover like cotton. The solid is washed two or three times with 1 to 2 mL of diethyl ether, and dried to give a hydrochloride with high purity. The N-(pyrazolylmethyl)

arylsulfonamide derivative represented by Chemical Formula 1, or an acid salt thereof is a novel compound. This acid salt compound, produced as a result of the reaction of the compound of Chemical Formula 1 with a typical organic or inorganic acid, may be in the form of hydrogen chloride salt, sulfuric acid salt, acetic acid salt, etc. Therefore, the compound, represented by Chemical Formula 2 as a novel intermediate, an acid salt thereof, and a preparation method thereof also fall within the scope of the present invention.

The N-(pyrazolylmethyl)arylsulfonamide derivatives represented by Chemical Formula 1, or a pharmaceutically acceptable salts thereof in accordance with the present invention has activity as a T-type calcium ion channel antagonist. Hence, a pharmaceutical composition comprising the novel compound of Chemical Formula 1 as an active ingredient is also within the scope of the present invention.

Comprising the N-(pyrazolylmethyl)arylsulfonamide derivatives represented by Chemical Formula 1 or a pharmaceutically acceptable salts thereof as an active ingredient, the composition of the present invention can be used as an agent effective for the therapy and prophylaxis of cerebral diseases, cardiac diseases, cancer, or pain diseases linked with T-type calcium ion channels. In detail, the diseases effectively treated or prevented by the novel compound of the present invention include cerebral diseases such as epilepsy, depression, dementia, sleep disorder, diabetes, obesity, etc.; heart diseases such as hypertension, cardiac arrhythmia, angina pectoris, myocardial infarction, and congestive heart failure; cancer, such as hepatic cancer, lung cancer, rectal cancer, prostate cancer, breast cancer, uterine cancer, esophageal cancer, brain cancer, etc.; pain syndrome such as chronic and acute pain, neuropathic pain, etc.

The pharmaceutical composition of the present invention may be formulated, together with a carrier, an additive and/or an excipient, into dosage forms typical in the pharmaceutical field. For example, oral dosage forms or non-oral dosage forms such as tablets, capsules, troches, solutions, suspensions, etc. may be used. In addition, the effective dosage of the compound represented by Chemical Formula 1 depends on various factors, including the patient's age, weight, gender, route of administration, state of health, severity of diseases, etc. Typically, the compound according to the present invention may be administered at a daily dose ranging from 0.01 to 400 mg. The compound may be administered in a single dose or may be divided into multiple doses per day according to the instructions of a physician or pharmacist.

A better understanding of the present invention may be obtained through the following examples which are set forth to illustrate, but are not to be construed as limiting the present invention.

EXAMPLES

Example 1

N-[(5-Isobutyl-1-phenyl-1H-pyrazol-3-yl)methyl]benzenesulfonamide (Compound 1)

To a solution of (5-isobutyl-3-aminomethyl-1-phenyl)pyrazole (290 mg, 1.26 mmol) in dichloromethane (3.0 mL) was added triethylamine (194 μL, 1.39 mmol) at 0° C. The solution was stirred for 5 min, and mixed with benzenesulfonyl chloride (170 μL, 1.33 mmol). Subsequently, the solution was warmed to room temperature, and stirred for 1 hr. Then, water and a saturated sodium hydrogen carbonate solution were added to the solution before extraction with dichloromethane. The organic layer thus obtained was dried over magnesium sulfate, concentrated in vacuo, and purified by column chromatography (Hexane:EtOAc=2:1) to afford the title compound (419 mg, 85.6%).

$^1$H NMR (300 MHz, CDCl$_3$) δ 7.86 (d, J=7.97 Hz, 2H), 7.56-7.37 (m, 6H), 7.25 (d, J=6.64 Hz, 2H), 6.01 (s, 1H), 5.59 (brs, 1H), 4.18 (d, J=5.96 Hz, 2H), 2.43 (d, J=7.17 Hz, 2H), 1.77-1.68 (m, 1H), 0.81 (d, J=6.62 Hz, 6H).

$^{13}$C NMR (75 MHz, CDCl$_3$) δ 147.9, 144.3, 140.0, 139.5, 132.5, 129.1, 129.0, 128.1 127.2, 125.7, 104.9, 41.1, 35.0, 28.3, 22.3

Example 2

N-[(5-Isobutyl-1-phenyl-1H-pyrazol-3-yl)methyl]-3-fluorobenzenesulfonamide (Compound 2)

To a solution of (5-isobutyl-3-aminomethyl-1-phenyl)pyrazole (182 mg, 0.792 mmol) in dichloromethane (3.0 mL) was added triethylamine (121 μL, 0.871 mmol) at 0° C. The solution was stirred for 5 min, and mixed with 3-fluorobenzenesulfonyl chloride (111 μL, 0.832 mmol). Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (262 mg, 85.5%).

$^1$H NMR (400 MHz, CDCl$_3$) δ 7.64-7.62 (m, 1H), 7.53-7.51 (m, 1H), 7.45-7.35 (m, 4H), 7.28-7.19 (m, 3H), 6.01 (s, 1H), 5.89 (t, J=5.81 Hz, 1H), 4.18 (d, J=5.87 Hz, 2H), 2.41 (d, J=7.19 Hz, 2H), 1.76-1.69 (m, 1H), 0.80 (d, J=6.61 Hz, 6H)

$^{13}$C NMR (100 MHz, CDCl$_3$) δ 163.5, 161.0, 147.7, 144.4, 142.2, 142.1, 139.5, 130.7, 130.7, 129.1, 128.2, 125.6, 123.0, 123.0, 119.7, 119.5, 114.6, 114.4, 104.9, 41.0, 35.0, 28.3, 22.3

Example 3

N-[(5-Isobutyl-1-phenyl-1H-pyrazol-3-yl)methyl]-3-chlorobenzenesulfonamide (Compound 3)

To a solution of (5-isobutyl-3-aminomethyl-1-phenyl)pyrazole (182 mg, 0.792 mmol) in dichloromethane (3.0 mL) was added triethylamine (122 μL, 0.872 mmol) at 0° C. The solution was stirred for 5 min, and mixed with 3-chlorobenzenesulfonyl chloride (117 μL, 0.832 mmol). Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (286 mg, 89.3%).

$^1$H NMR (400 MHz, CDCl$_3$) δ 7.83-7.82 (m, 1H), 7.74-7.71 (m, 1H), 7.50-7.35 (m, 5H), 7.27-7.24 (m, 2H), 6.01 (s, 1H), 5.70 (brs, 1H), 4.20 (d, J=5.86 Hz, 2H), 2.42 (d, J=7.18 Hz, 2H), 1.77-1.70 (m, 1H), 0.81 (d, J=6.63 Hz, 6H)

$^{13}$C NMR (100 MHz, CDCl$_3$) δ 147.6, 144.4, 141.8, 139.5, 135.0, 132.5, 130.2, 129.1, 128.2, 127.3, 125.6, 125.3, 104.9, 41.1, 35.0, 28.3, 22.4

Example 4

N-[(5-Isobutyl-1-phenyl-1H-pyrazol-3-yl)methyl]-4-methylbenzenesulfonamide (Compound 4)

To a solution of (5-isobutyl-3-aminomethyl-1-phenyl) pyrazole (57.5 mg, 0.251 mmol) in dichloromethane (1.0 mL) was added triethylamine (38.4 μL, 0.276 mmol) at 0° C. The solution was stirred for 5 min, and mixed with a solution of p-toluenesulfonyl chloride (50.5 mg, 0.263 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (87.7 mg, 91.2%).

$^1$H NMR (400 MHz, CDCl$_3$) δ 7.74 (d, J=8.24 Hz, 2H), 7.44-7.37 (m, 3H), 7.27-7.24 (m, 4H), 6.00 (s, 1H), 5.43 (brs, 1H), 4.16 (d, J=5.92 Hz, 2H), 2.42 (d, J=7.20 Hz, 2H), 2.39 (s, 3H), 1.76-1.69 (m, 1H), 0.81 (d, J=6.64 Hz, 6H)

$^{13}$C NMR (100 MHz, CDCl$_3$) δ 148.0, 144.3, 143.2, 139.6, 137.0, 129.6, 129.1, 128.1, 127.3, 125.6, 104.9, 41.1, 35.0, 28.3, 22.3, 21.5

Example 5

N-[(5-Isobutyl-1-phenyl-1H-pyrazol-3-yl)methyl]-4-iodobenzenesulfonamide (Compound 5)

To a solution of (5-isobutyl-3-aminomethyl-1-phenyl) pyrazole (48.7 mg, 0.212 mmol) in dichloromethane (1.0 mL) was added triethylamine (32.6 μL, 0.234 mmol) at 0° C. The solution was stirred for 5 min, and mixed with a solution of 4-iodobenzenesulfonyl chloride (68.2 mg, 0.223 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (86.3 mg, 82.0%).

$^1$H NMR (400 MHz, CDCl$_3$) δ 7.76 (d, J=8.16 Hz, 2H), 7.53 (d, J=8.24 Hz, 2H), 7.46-7.38 (m, 3H), 7.23 (d, J=7.60 Hz, 2H), 5.95 (s, 1H), 5.72 (brs, 1H), 4.18 (d, J=5.80 Hz, 2H), 2.40 (d, J=7.16 Hz, 2H), 1.75-1.68 (m, 1H), 0.81 (d, J=6.60 Hz, 6H)

$^{13}$C NMR (100 MHz, CDCl$_3$) δ 147.6, 144.4, 139.9, 139.5, 138.1, 129.2, 128.7, 128.2, 125.7, 104.8, 99.7, 41.0, 35.0, 28.3, 22.4

Example 6

N-[(5-Isobutyl-1-phenyl-1H-pyrazol-3-yl)methyl]-4-tert-butylbenzenesulfonamide (Compound 6)

To a solution of (5-isobutyl-3-aminomethyl-1-phenyl) pyrazole (52.6 mg, 0.229 mmol) indichloromethane (1.0 mL) was added triethylamine (35.2 μL, 0.252 mmol) at 0° C. The solution was stirred for 5 min, and mixed with a solution of 4-tert-butylbenzenesulfonyl chloride (56.5 mg, 0.241 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (65.7 mg, 67.3%)

$^1$H NMR (400 MHz, CDCl$_3$) δ 7.80 (d, J=8.52 Hz, 2H), 7.49 (d, J=8.52 Hz, 2H), 7.45-7.37 (m, 3H), 7.28-7.25 (m, 2H), 6.04 (s, 1H), 5.26 (brs, 1H), 4.18 (d, J=5.88 Hz, 2H), 2.43 (d, J=7.16 Hz, 2H), 1.78-1.70 (m, 1H), 1.33 (s, 9H), 0.82 (d, J=6.64 Hz, 6H)

$^{13}$C NMR (100 MHz, CDCl$_3$) δ 156.3, 148.0, 144.3, 139.6, 136.8, 129.1, 128.1, 127.1, 126.0, 125.6, 104.9, 41.2, 35.1, 35.1, 31.1, 28.3, 22.4

Example 7

N-[(5-Isobutyl-1-phenyl-1H-pyrazol-3-yl)methyl]benzylsulfonamide (Compound 7)

To a solution of (5-isobutyl-3-aminomethyl-1-phenyl) pyrazole (48.7 mg, 0.212 mmol) in dichloromethane (1.5 mL) was added triethylamine (32.6 μL, 0.234 mmol) at 0° C. The solution was stirred for 5 min, and mixed with a solution of phenylmethanesulfonyl chloride (43.0 mg, 0.223 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (64.2 mg, 78.9%).

$^1$H NMR (400 MHz, CDCl$_3$) δ 7.49-7.45 (m, 2H), 7.42-7.38 (m, 1H), 7.36-7.32 (m, 2H), 7.26 (brs, 5H), 6.17 (s, 1H), 4.97 (brs, 1H), 4.25 (s, 2H), 4.19 (d, J=5.88 Hz, 2H), 2.49 (d, J=7.16 Hz, 2H), 1.84-1.77 (m, 1H), 0.85 (d, J=6.60 Hz, 6H)

$^{13}$C NMR (100 MHz, CDCl$_3$) δ 148.7, 144.6, 139.7, 130.8, 129.4, 129.2, 128.7, 128.6, 128.2, 125.7, 105.1, 59.1, 41.3, 35.1, 28.4, 22.4

Example 8

N-[(5-Isobutyl-1-phenyl-1H-pyrazol-3-yl)methyl]naphthalene-1-sulfonamide (Compound 8)

To a solution of (5-isobutyl-3-aminomethyl-1-phenyl) pyrazole (51.1 mg, 0.223 mmol) in dichloromethane (1.0 mL) was added triethylamine (34.2 μL, 0.245 mmol) at 0° C. The solution was stirred for 5 min, and mixed with a solution of naphthalene-1-sulfonyl chloride (53.5 mg, 0.234 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (82.9 mg, 88.7%).

$^1$H NMR (400 MHz, CDCl$_3$) δ 8.67 (d, J=8.40 Hz, 1H), 8.28 (d, J=7.34 Hz, 1H), 8.01 (d, J=8.21 Hz, 1H), 7.90 (d, J=8.02 Hz, 1H), 7.62-7.53 (m, 2H), 7.48 (t, J=7.42 Hz, 1H), 7.40-7.31 (m, 3H), 7.11 (d, J=8.10 Hz, 2H), 5.77 (s, 1H), 5.56 (brs, 1H), 4.17 (d, J=5.92 Hz, 2H), 2.29 (d, J=7.16 Hz, 2H), 1.64-1.57 (m, 1H), 0.73 (d, J=6.60 Hz, 6H)

$^{13}$C NMR (100 MHz, CDCl$_3$) δ 147.9, 144.1, 139.5, 134.9, 134.2, 134.1, 129.6, 129.0, 129.0, 128.3, 128.0, 126.8, 125.6, 124.6, 124.1, 104.7, 41.2, 34.9, 28.2, 22.3

Example 9

N-[(5-Isobutyl-1-phenyl-1H-pyrazol-3-yl)methyl] naphthalene-2-sulfonamide. (Compound 9)

To a solution of (5-isobutyl-3-aminomethyl-1-phenyl) pyrazole (51.1 mg, 0.223 mmol) in dichloromethane (1.0 mL) was added triethylamine (34.2 μL, 0.245 mmol) at 0° C. The solution was stirred for 5 min, and mixed with a solution of naphthalene-2-sulfonyl chloride (53.1 mg, 0.234 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (82.7 mg, 88.5%).

$^1$H NMR (400 MHz, CDCl$_3$) δ 8.43 (s, 1H), 7.92-7.80 (m, 4H), 7.64-7.54 (m, 2H), 7.37-7.29 (m, 3H), 7.11-7.09 (m, 2H), 5.92 (s, 1H), 5.63 (brs, 1H), 4.24 (d, J=5.96 Hz, 2H), 2.27 (d, J=7.15 Hz, 2H), 1.62-1.55 (m, 1H), 0.72 (d, J=6.60 Hz, 6H)

$^{13}$C NMR (100 MHz, CDCl$_3$) δ 147.9, 144.2, 139.5, 136.9, 134.8, 132.1, 129.3, 129.2, 129.0, 128.7, 128.5, 128.0, 127.8, 127.4, 125.6, 122.7, 104.8, 41.2, 34.9, 28.2, 22.3

Example 10

N-[(5-Isobutyl-1-phenyl-1H-pyrazol-3-yl)methyl] quinoline-8-sulfonamide (Compound 10)

To a solution of (5-isobutyl-3-aminomethyl-1-phenyl) pyrazole (44.7 mg, 0.195 mmol) in dichloromethane (1.5 mL) was added triethylamine (29.9 μL, 0.214 mmol) at 0° C. The solution was stirred for 5 min, and mixed with a solution of quinoline-8-sulfonyl chloride (46.5 mg, 0.205 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=2:1→1:1) to afford the title compound (73.2 mg, 89.3%).

$^1$H NMR (400 MHz, CDCl$_3$) δ 8.95-8.94 (m, 1H), 8.43 (d, J=7.26 Hz, 1H), 8.21 (d, J=8.29 Hz, 1H), 8.00 (d, J=8.20 Hz, 1H), 7.60 (t, J=7.46 Hz, 1H), 7.49-7.46 (m, 1H), 7.40-7.31 (m, 3H), 7.09 (d, J=7.98 Hz, 2H), 6.82 (t, J=6.32 Hz, 1H), 5.92 (s, 1H), 4.20 (d, J=6.36 Hz, 2H), 2.30 (d, J=7.12 Hz, 2H), 1.67-1.59 (m, 1H), 0.75 (d, J=6.52 Hz, 6H)

$^{13}$C NMR (100 MHz, CDCl$_3$) δ 151.1, 148.0, 143.7, 143.3, 139.5, 136.8, 136.2, 133.2, 130.9, 129.0, 128.7, 127.9, 125.5, 125.4, 122.1, 105.2, 41.6, 34.9, 28.2, 22.3

Example 11

N-[(5-Isobutyl-1-phenyl-1H-pyrazol-3-yl)methyl]-(2-fluoro-5-methyl)benzenesulfonamide (Compound 11)

To a solution of (5-isobutyl-3-aminomethyl-1-phenyl) pyrazole (45.7 mg, 0.199 mmol) in dichloromethane (1.5 mL) was added triethylamine (30.6 μL, 0.219 mmol) at 0° C. The solution was stirred for 5 min, and mixed with a solution of 2-fluoro-5-methylbenzenesulfonyl chloride (44.3 mg, 0.209 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (72.3 mg, 90.4%).

$^1$H NMR (400 MHz, CDCl$_3$) δ 7.70 (d, J=6.72 Hz, 1H), 7.46-7.36 (m, 3H), 7.31-7.26 (m, 3H), 7.00 (t, J=8.60 Hz, 1H), 6.02 (s, 1H), 5.45 (brs, 1H), 4.25 (d, J=5.96 Hz, 2H), 2.42 (d, J=7.12 Hz, 2H), 2.34 (s, 3H), 1.76-1.68 (m, 1H), 0.82 (d, J=6.60 Hz, 6H)

$^{13}$C NMR (100 MHz, CDCl$_3$) δ 158.3, 155.8, 147.7, 144.3, 139.6, 135.2, 135.1, 134.2, 130.4, 129.1, 128.1, 127.5, 127.3, 125.6, 116.6, 116.4, 104.8, 41.2, 35.0, 28.3, 22.4, 20.6

Example 12

N-[(5-Isobutyl-1-phenyl-1H-pyrazol-3-yl)methyl]-(2-methyl-3-chloro)benzenesulfonamide (Compound 12)

To a solution of (5-isobutyl-3-aminomethyl-1-phenyl) pyrazole (45.1 mg, 0.197 mmol) in dichloromethane (1.5 mL) was added triethylamine (30.2 μL, 0.216 mmol) at 0° C. The solution was stirred for 5 min, and mixed with a solution of 3-chloro-2-methylbenzenesulfonyl chloride (46.5 mg, 0.207 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (69.6 mg, 84.7%).

$^1$H NMR (400 MHz, CDCl$_3$) δ 7.95 (d, J=7.95 Hz, 1H), 7.52 (d, J=8.00 Hz, 1H), 7.47-7.37 (m, 3H), 7.27 (d, J=7.95 Hz, 2H), 7.21 (t, J=7.95 Hz, 1H), 5.87 (s, 1H), 5.57 (brs, 1H), 4.20 (d, J=5.80 Hz, 2H), 2.64 (s, 3H), 2.40 (d, J=7.16 Hz, 2H), 1.74-1.68 (m, 1H), 0.80 (d, J=6.61 Hz, 6H)

$^{13}$C NMR (100 MHz, CDCl$_3$) δ 147.7, 144.3, 140.3, 139.5, 136.8, 135.2, 133.4, 129.2, 128.2, 128.2, 126.5, 125.7, 104.7, 40.9, 35.0, 28.3, 22.4, 16.9

Example 13

N-[(5-Isobutyl-1-phenyl-1H-pyrazol-3-yl)methyl]-2,6-difluorobenzenesulfonamide (Compound 13)

To a solution of (5-isobutyl-3-aminomethyl-1-phenyl) pyrazole (46.6 mg, 0.203 mmol) in dichloromethane (2.0 mL) was added triethylamine (31.2 μL, 0.224 mmol) at 0° C. The solution was stirred for 5 min, and mixed with 2,6-difluorobenzenesulfonyl chloride (28.6 μL, 0.213 mmol). Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (67.7 mg, 82.2%).

$^1$H NMR (400 MHz, CDCl$_3$) δ 7.47-7.39 (m, 4H), 7.28-7.26 (m, 2H), 6.94 (t, J=8.60 Hz, 2H), 6.07 (s, 1H), 5.73 (brs, 1H), 4.36 (d, J=5.94 Hz, 2H), 2.41 (d, J=7.16 Hz, 2H), 1.77-1.71 (m, 1H), 0.82 (d, J=6.62 Hz, 6H)

$^{13}$C NMR (100 MHz, CDCl$_3$) δ 160.8, 158.3, 147.4, 144.3, 139.5, 134.2, 134.1, 134.0, 129.1, 128.1, 125.6, 118.3, 113.0, 112.8, 112.8, 104.9, 41.2, 35.0, 28.3, 22.48

Example 14

N-[(5-Isobutyl-1-phenyl-1H-pyrazol-3-yl)methyl]-2,6-dichlorobenzenesulfonamide (Compound 14)

To a solution of (5-isobutyl-3-aminomethyl-1-phenyl)pyrazole (42.6 mg, 0.186 mmol) in dichloromethane (2.0 mL) was added triethylamine (28.5 μL, 0.204 mmol) at 0° C. The solution was stirred for 5 min, and mixed with a solution of 2,6-dichlorobenzenesulfonyl chloride (48.3 mg, 0.195 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=3:1→2:1) to afford the title compound (64.9 mg, 79.7%).

$^1$H NMR (400 MHz, CDCl$_3$) δ 7.47-7.38 (m, 5H), 7.28-7.24 (m, 3H), 6.01 (s, 1H), 6.00 (brs, 1H), 4.32 (d, J=6.04 Hz, 2H), 2.39 (d, J=7.14 Hz, 2H), 1.75-1.69 (m, 1H), 0.81 (d, J=6.64 Hz, 6H)

$^{13}$C NMR (100 MHz, CDCl$_3$) δ 147.3, 144.2, 139.6, 135.7, 135.0, 132.2, 131.2, 129.1, 128.1, 125.5, 104.9, 41.3, 35.0, 28.3, 22.4

Example 15

2-Phenylethanesulfonyl chloride

To a solution of N-chlorosuccinimide (534 mg, 4.00 mmol) in 2M HCl—CH$_3$CN (267.4 mL-1.34 mL, 3 v/w to NCS) was added a solution of 2-phenylethanethiol (134 μL, 1.00 mmol) in CH$_3$CN (267.4 μL, 0.5 v/w to NCS) at 10° C. Thirty min later, diethyl ether was added to the solution, followed by three rounds of extraction with brine. The organic layer thus formed was dried over sodium sulfate, filtered, and concentrated in vacuo to afford the title compound (195.5 mg, 95.4%).

$^1$H NMR (300 MHz, CDCl$_3$) δ 7.43-7.27 (m, 5H), 3.98-3.92 (m, 3H), 3.41-3.35 (m, 1H)

Example 16

N-[(5-isobutyl-1-phenyl-1H-pyrazol-3-yl)methyl]-2-phenylethanesulfonamide (Compound 19)

To a solution of (5-isobutyl-3-aminomethyl-1-phenyl)pyrazole (121 mg, 0.528 mmol) in dichloromethane (1.5 mL) was added triethylamine (80.9 μL, 0.580 mmol) at 0° C. The solution was stirred for 5 min, and mixed with a solution of 2-phenylethanesulfonyl chloride (113 mg, 0.553 mmol) in dichloromethane. Subsequently, the solution was warmed to room temperature, and stirred for 1 hr. Then, water and a saturated sodium hydrogen carbonate solution were added to the solution before extraction with dichloromethane. The organic layer thus formed was dried over magnesium sulfate, concentrated in vacuo, and purified by column chromatography (Hexane:EtOAc=2:1) to afford the title compound (187 mg, 89.3%).

$^1$H NMR (300 MHz, CDCl$_3$) δ 7.50-7.42 (m, 3H), 7.34-7.24 (m, 5H), 7.13-7.10 (m, 2H), 6.22 (s, 1H), 5.40 (t, J=5.94 Hz, 1H), 4.38 (d, J=5.97 Hz, 2H), 3.33-3.27 (m, 2H), 3.13-3.07 (m, 2H), 2.51 (d, J=7.20 Hz, 2H), 1.89-1.75 (m, 1H), 0.87 (d, J=6.63 Hz, 6H)

$^{13}$C NMR (100 MHz, CDCl$_3$) δ 148.7, 144.6, 139.6, 138.1, 129.2, 128.7, 128.3, 128.2, 126.8, 125.8, 105.0, 54.2, 40.9, 35.1, 29.8, 28.4, 22.4

Example 17

5-Methyl hexan-3-ol

To a solution of ethyl magnesium bromide (1M in THF, 25.0 mL, 25.0 mmol) in diethyl ether (5.0 mL) was slowly added a solution of isovaleric anhydride (2.16 mL, 20.0 mmol) in diethyl ether. The reaction mixture was refluxed for 3 hrs and then cooled to 0° C. before the addition of 3N HCl (8.3 mL) thereto. After extraction with diethyl ether, the organic layer was washed once with a saturated sodium metabisulfite solution, and then twice with saturated sodium hydrogen carbonate solution. The organic layer was dried over magnesium sulfate, and concentrated in a water bath (60° C.) only using a rotary evaporator to afford the title compound (2.30 g, 100%).

$^1$H NMR (400 MHz, CDCl$_3$) δ 3.67-3.54 (m, 1H), 1.82-1.74 (m, 1H), 1.54-1.39 (m, 2H), 1.38-1.27 (m, 2H), 0.96-0.91 (m, 9H)

Example 18

5-Methyl hexan-3-one

Pyridinium chlorochromate (8.61 g, 39.9 mmol) and silica gel (8.61 g) were dried in vacuo and dissolved in dichloromethane (10.0 mL). This solution was mixed with a solution of 5-methylhexan-3-ol in dichloromethane by stirring for 2.5 hrs. After filtration through silica gel, concentration in a water bath (60° C.) only using a rotary evaporator afforded the title compound (2.18 g, 95%).

$^1$H NMR (400 MHz, CDCl$_3$) δ 2.40 (q, J=7.32 Hz, 2H), 2.28 (d, J=6.96 Hz, 2H), 2.18-2.10 (m, 1H), 1.05 (t, J=7.32 Hz, 3H), 0.91 (d, J=6.60 Hz, 6H)

Example 19

(Z)-Ethyl 2-hydroxy-3,6-dimethyl-4-oxohept-2-enoate

To a solution of lithium bis(trimethylsilyl)amide (1M in THF, 13.0 mL, 13.0 mmol) in diethyl ether (65 mL) was added 5-methylhexan-3-one (1.49 g, 13.0 mmol) in diethyl ether at −78° C. After stirring for 45 min, diethyl oxalate (1.94 mL, 14.3 mmol) was added. One hour later, the reaction mixture was elevated to room temperature, and stirred for about 18 hrs. After neutralization with 1N HCl, water was added. Extraction with diethyl ether gave an organic layer that was then dried over magnesium sulfate, concentrated in vacuo, and dried to afford a crude title compound.

$^1$H NMR (400 MHz, CDCl$_3$) δ 4.20 (m, 2H), 2.90 (2H, d), 2.42 (s, 3H), 1.98 (t, 1H), 1.28 (t, 3H), 0.91 (d, 6H)

Example 20

Ethyl 5-isobutyl-4-methyl-1-phenyl-1H-pyrazole-3-carboxylate

To a solution of (Z)-ethyl 2-hydroxy-3,6-dimethyl-4-oxohept-2-enoate (1.94 g, 9.06 mmol) in ethanol (31 mL) was added phenyl hydrazine (890 μL, 9.06 mmol). Two hours later, the solution was mixed 1N HCl while stirring overnight. The solvent was removed, and water was added, followed by extraction with dichloromethane. The organic layer thus formed was dried over magnesium sulfate, filtered, concentrated in vacuo, and purified by column chromatography (Hexane:EtOAc=12:1→6:1) to afford 540 mg of the title compound.

$^1$H NMR (400 MHz, CDCl$_3$) δ 7.46-7.38 (m, 5H), 4.42 (q, J=7.12 Hz, 2H), 2.51 (d, J=7.48 Hz, 2H), 2.30 (s, 3H), 1.60-1.52 (m, 1H), 1.41 (t, J=7.12 Hz, 3H), 0.74 (d, J=6.68 Hz, 6H)

Example 21

5-Isobutyl-4-methyl-1-phenyl-1H-pyrazole-3-carbaldehyde

Ethyl 5-isobutyl-4-methyl-1-phenyl-1H-pyrazole-3-carboxylate (273 mg, 0.953 mmol) was dried in vacuo, and then dissolved in dichloromethane (1.0 mL). At −78° C., diisobutylaluminum hydride (1M in hexane, 2.86 mL, 2.86 mmol) was added to the solution, and then stirred for 1 hr. After addition of methanol and 1N HCl thereto, the reaction mixture was warmed to room temperature, mixed with water, and extracted with dichloromethane. The organic layer thus formed was dried over magnesium sulfate, filtered, concentrated in vacuo, and purified by column chromatography (Hexane:EtOAc=10:1) to afford the title compound (196 mg, 85.0%).

$^1$H NMR (400 MHz, CDCl$_3$) δ 10.1 (s, 1H), 7.52-7.40 (m, 5H), 2.54 (d, J=7.44 Hz, 2H), 2.32 (s, 3H), 1.67-1.59 (m, 1H), 0.75 (d, J=6.68 Hz, 6H)

Example 22

3-(Hydroxyamino)methyl-5-isobutyl-4-methyl-1-phenylpyrazole

To a solution of hydroxylamine hydrogen chloride (61.2 mg, 0.880 mmol) in dichloromethane (1.0 mL) was added triethylamine (123 μL, 0.880 mmol). After stirring for 5 min, the pH of the solution was measured. A solution of 5-isobutyl-4-methyl-1-phenyl-1H-pyrazole-3-carbaldehyde (194 mg, 0.800 mmol) in dichloromethane was added. The resulting reaction mixture was stirred for 3.5 hrs, added with water, and extracted with dichloromethane. The organic layer was dried over magnesium sulfate, concentrated in vacuo, and dried to afford the title compound (196 mg, 95.1%).

$^1$H NMR (400 MHz, CDCl$_3$) δ 8.29 (s, 1H), 7.47-7.37 (m, 5H), 2.53 (d, J=7.44 Hz, 2H), 2.21 (s, 3H), 1.68-1.60 (m, 1H), 0.74 (d, J=6.68 Hz, 6H)

Example 23

(5-Isobutyl-4-methyl-1-phenyl-1H-pyrazol-3-yl)methaneamine

After being dried in vacuo, 3-(hydroxyamino)methyl-5-isobutyl-4-methyl-1-phenylpyrazole (195 mg, 0.757 mmol) was dissolved in a mixed solvent of diethyl ether (1.0 mL) and tetrahydrofuran (2.0 mL), and added with lithium aluminum hydride (1M in diethyl ether, 1.67 mL, 1.67 mmol) at 0° C. At this temperature, stirring was conducted for 30 min before at room temperature for 3 hrs. The temperature was reduced again to 0° C. to carefully add sodium sulfate hydrate to the solution. The reaction mixture was filtered through celite and sodium sulfate, concentrated in vacuo, and dried to afford the title compound (178 mg, 96.5%).

$^1$H NMR (400 MHz, CDCl$_3$) δ 7.46-7.34 (m, 5H), 3.87 (s, 2H), 2.51 (d, J=7.40 Hz, 2H), 2.04 (s, 3H), 1.63-1.55 (m, 1H), 0.75 (d, J=6.64 Hz, 6H)

Example 24

N-[(5-Isobutyl-4-methyl-1-phenyl-1H-pyrazol-3-yl)methyl]benzenesulfonamide (Compound 15)

To a solution of (5-isobutyl-4-methyl-1-phenyl-1H-pyrazol-3-yl)methaneamine (55.7 mg, 0.229 mmol) in dichloromethane (2.0 mL) was added triethylamine (35.1 μL, 0.252 mmol) at 0° C. The solution was stirred for 5 min, and mixed with benzenesulfonyl chloride (30.7 μL, 0.240 mmol). After stirring for 1 hr at room temperature, water and an aqueous saturate sodium hydrogen carbonate solution were added to the reaction mixture that was then extracted with dichloromethane. The organic layer thus formed was dried over magnesium sulfate, concentrated in vacuo, and purified by column chromatography (Hexane:EtOAc=3:1) to afford the title compound (77.1 mg, 87.8%).

$^1$H NMR (400 MHz, CDCl$_3$) δ 7.86-7.84 (m, 2H), 7.53-7.50 (m, 1H), 7.46-7.35 (m, 5H), 7.24-7.22 (m, 2H), 5.53 (brs, 1H), 4.12 (d, J=5.68 Hz, 2H), 2.44 (d, J=7.40 Hz, 2H), 1.94 (s, 3H), 1.58-1.50 (m, 1H), 0.69 (d, J=6.63 Hz, 6H)

$^{13}$C NMR (100 MHz, CDCl$_3$) δ 147.8, 141.1, 140.0, 139.7, 132.5, 129.1, 128.9, 128.0, 127.1, 125.7, 113.1, 39.7, 33.2, 28.4, 22.2, 8.08

Example 25

N-[(5-Isobutyl-4-methyl-1-phenyl-1H-pyrazol-3-yl)methyl]naphthalene-2-sulfonamide (Compound 16)

To a solution of (5-isobutyl-4-methyl-1-phenyl-1H-pyrazol-3-yl)methaneamine (50.7 mg, 0.208 mmol) in dichloromethane (2.0 mL) was added triethylamine (31.9 μL, 0.229 mmol) at 0° C. The solution was stirred for 5 min, and added with naphthalene-2-sulfonyl chloride (49.7 mg, 0.219 mmol) in dichloromethane. The reaction mixture was stirred for 1 hr at room temperature, mixed with water and an aqueous saturate sodium hydrogen carbonate solution, and then extracted with dichloromethane. The organic layer thus formed was dried over magnesium sulfate, filtered in vacuo, and purified by column chromatography (Hexane:EtOAc=3:1) to afford the title compound (78.2 mg, 86.6%).

$^1$H NMR (400 MHz, CDCl$_3$) δ 8.67 (d, J=8.40 Hz, 1H), 8.27 (d, J=7.28 Hz, 1H), 7.99 (d, J=8.20 Hz, 1H), 7.88 (d, J=7.88 Hz, 1H), 7.61-7.51 (m, 2H), 7.49-7.45 (m, 1H), 7.39-7.30 (m, 3H), 7.11-7.09 (m, 2H), 5.62 (brs, 1H), 4.11 (d, J=5.60 Hz, 2H), 2.35 (d, J=7.40 Hz, 2H), 1.80 (s, 3H), 1.51-1.45 (m, 1H), 0.63 (d, J=6.64 Hz, 6H)

$^{13}$C NMR (100 MHz, CDCl$_3$) δ 145.8, 140.9, 140.0, 134.7, 134.2, 134.1, 129.4, 129.0, 128.3, 128.2, 127.9, 126.8, 125.6, 124.6, 124.1, 112.9, 39.8, 33.2, 28.3, 22.2, 7.97

Example 26

Ethyl (Z)-3-ethyl-2-hydroxy-6-methyl-4-oxohept-2-enoate

To a solution of lithium bis(trimethylsilyl)amide (1M in THF, 13.1 mL, 13.1 mmol) in diethyl ether (52 mL) was added 2-methyl-4-heptanone (2.05 mL, 13.0 mmol) at −78° C. The solution was stirred for 45 min, and mixed with diethyl oxalate (1.85 mL, 13.7 mmol) for 1 hr. Thereafter, the reaction mixture was warmed to room temperature and stirred for an additional 18 hrs. It was acidified with 1N HCl, added with water, and extracted with diethyl ether. The organic layer thus obtained was dried over magnesium sulfate, and then concentrated in a water bath (65° C.) only using a rotary evaporator to afford the title compound.

$^1$H NMR (400 MHz, CDCl$_3$) δ 4.21 (q, 2H), 2.90 (d, 2H), 2.42 (q, 2H), 1.96 (t, 1H), 1.26 (t, 3H), 1.00 (t, 3H), 0.91 (d, 6H)

Example 27

Ethyl 4-ethyl-5-isobutyl-1-phenyl-1H-pyrazole-3-carboxylate

To a solution of ethyl (Z)-3-ethyl-2-hydroxy-6-methyl-4-oxohept-2-enoate (2.97 g, 13.0 mmol) in ethanol (40 mL) was added phenyl hydrazine (1.28 mL, 13.0 mmol). One hour later, 1N HCl was added to the solution that was then stirred at 80° C. for 3 hrs. After removal of the solvent, the reaction mixture was added with water and extracted with dichloromethane. The organic layer thus formed was dried over magnesium sulfate, filtered in vacuo, and purified by column chromatography (Hexane:EtOAc=15:1→5:1) to afford 607 mg of the title compound.

$^1$H NMR (400 MHz, CDCl$_3$) δ 7.46-7.39 (m, 5H), 4.42 (q, J=7.12 Hz, 2H), 2.75 (q, J=7.44 Hz, 2H), 2.53 (d, J=7.56 Hz, 2H), 1.60-1.52 (m, 1H), 1.41 (t, J=7.12 Hz, 3H), 1.20 (t, J=7.44 Hz, 3H), 0.73 (d, J=6.64 Hz, 6H)

Example 28

4-Ethyl-5-isobutyl-1-phenyl-1H-pyrazole-3-carbaldehyde

Dried ethyl 4-ethyl-5-isobutyl-1-phenyl-1H-pyrazole-3-carboxylate (454 mg, 1.51 mmol) was dissolved in dichloromethane (2.0 mL), and diisobutylaluminum hydride (1M in hexane, 4.53 mL, 4.53 mmol) was added at −78° C. to the solution. It was stirred for 1.5 hrs, and mixed with methanol and 1N HCl. After the temperature of the reaction mixture was elevated to room temperature, it was added with water and extracted with dichloromethane. The organic layer thus formed was dried over magnesium sulfate, filtered, and purified by column chromatography (Hexane:EtOAc=10:1) to afford the title compound (332 mg, 85.8%).

$^1$H NMR (400 MHz, CDCl$_3$) δ 10.1 (s, 1H), 7.52-7.41 (m, 5H), 2.74 (q, J=7.40 Hz, 2H), 2.55 (d, J=7.52 Hz, 2H), 1.62-1.54 (m, 1H), 1.21 (t, J=7.40 Hz, 3H), 0.74 (d, J=6.64 Hz, 6H)

Example 29

4-Ethyl-3-(hydroxyamino)methyl-5-isobutyl-1-phenylpyrazole

To a solution of hydroxylamine hydrogen chloride (82.5 mg, 1.18 mmol) in dichloromethane (2.5 mL) was added triethylamine (165 μL, 1.18 mmol). After stirring for 5 min, the pH of the solution was measured. A solution of dichloromethane in 4-ethyl-5-isobutyl-1-phenyl-1H-pyrazole-3-carbaldehyde (276 mg, 1.08 mmol) was added. The resulting reaction mixture was stirred for 5 hrs, added with water, and extracted with dichloromethane. The organic thus obtained was dried over magnesium sulfate, filtered, concentrated in vacuo, and purified to afford the title compound (284 mg, 97.0%).

$^1$H NMR (400 MHz, CDCl$_3$) δ 8.27 (s, 1H), 7.49-7.36 (m, 5H), 7.17 (s, 1H), 2.65 (q, J=7.44 Hz, 2H), 2.55 (d, J=7.52 Hz, 2H), 1.63-1.52 (m, 1H), 1.17 (t, J=7.44 Hz, 3H), 0.74 (d, J=6.60 Hz, 6H)

Example 30

(4-Ethyl-5-isobutyl-1-phenyl-1H-pyrazol-3-yl)methaneamine

Dried 4-ethyl-3-(hydroxyamino)methyl-5-isobutyl-1-phenylpyrazole (282 mg, 1.04 mmol) was dissolved in a mixed solvent of diethyl ether (1.4 mL) and tetrahydrofuran (2.7 mL), and lithium aluminum hydride (1M in diethyl ether, 2.29 mL, 2.29 mmol) was added at −0° C. to the solution. It was stirred for 30 min before for 30 min at room temperature. The temperature was reduced again to 0° C. to carefully add sodium sulfate hydrate to the solution. The reaction mixture was filtered through celite and sodium sulfate, concentrated in vacuo, and dried to afford the title compound (266 mg, 99.3%).

$^1$H NMR (400 MHz, CDCl$_3$) δ 7.45-7.34 (m, 5H), 3.89 (s, 2H), 2.52 (d, J=7.50 Hz, 2H), 2.48 (q, J=7.57 Hz, 2H), 1.60-1.52 (m, 1H), 1.17 (t, J=7.57 Hz, 3H), 0.73 (d, J=6.63 Hz, 6H)

Example 31

N-[(5-Isobutyl-4-ethyl-1-phenyl-1H-pyrazol-3-yl)methyl]benzenesulfonamide (Compound 17)

To a solution of (4-ethyl-5-isobutyl-1-phenyl-1H-pyrazol-3-yl)methaneamine (50.0 mg, 0.194 mmol) in dichloromethane (2.0 mL) was added triethylamine (29.8 μL, 0.214 mmol) at 0° C. The solution was stirred for 5 min, and mixed with benzenesulfonyl chloride (26.1 μL, 0.204 mmol). Thereafter, the reaction mixture was warmed to room temperature and stirred for an additional 1 hr. It was mixed with water and an aqueous saturate sodium hydrogen carbonate solution, and extracted with dichloromethane. The organic layer thus formed was dried over magnesium sulfate, filtered, and purified by column chromatography (Hexane:EtOAc=3:1) to afford the title compound (69.6 mg, 90.1%).

$^1$H NMR (400 MHz, CDCl$_3$) δ 7.87-7.85 (m, 2H), 7.54-7.50 (m, 1H), 7.47-7.36 (m, 5H), 7.26-7.24 (m, 2H), 5.45 (brs, 1H), 4.14 (d, J=5.60 Hz, 2H), 2.46 (d, J=7.52 Hz, 2H), 2.40 (q, J=7.60 Hz, 2H), 1.56-1.48 (m, 1H), 1.10 (t, J=7.60 Hz, 3H), 0.68 (d, J=6.64 Hz, 6H)

$^{13}$C NMR (100 MHz, CDCl$_3$) δ 145.4, 140.6, 140.2, 139.6, 132.5, 129.1, 129.0, 128.0, 127.2, 125.7, 119.6, 39.8, 33.2, 28.1, 22.3, 16.4, 15.5

Example 32

(5-Isobutyl-1-phenyl-1H-pyrazol-3-yl)methanol

Dried ethyl 5-isobutyl-1-phenyl-1H-pyrazole-3-carboxylate (1.76 g, 6.47 mmol) was added to a mixed solvent of diethyl ether (2.0 mL) and dichloromethane (3.0 mL), and lithium aluminum hydride (1M in diethyl ether, 14.2 mL, 14.2 mmol) was added at 0° C. to the solution. It was stirred for 30 min before for 30 min at room temperature. The temperature was reduced again to 0° C. to carefully add water to the solution, followed by filtration. The filtrate was added with an aqueous saturate sodium hydrogen carbonate solution, and extracted with dichloromethane. The organic layer thus obtained was dried over magnesium sulfate, filtered, and concentrated in vacuo to dryness to afford the title compound (1.48 g, 99.2%).

$^1$H NMR (400 MHz, CDCl$_3$) δ 7.51-7.39 (m, 5H), 6.22 (s, 1H), 4.74 (d, J=5.92 Hz, 2H), 2.53 (d, J=7.17 Hz, 2H), 2.03 (brs, 1H), 1.88-1.80 (m, 1H), 0.88 (d, J=6.62 Hz, 6H)

Example 33

3-(Azidomethyl)-5-isobutyl-1-phenyl-1H-pyrazole

To a solution of (5-isobutyl-1-phenyl-1H-pyrazol-3-yl)methanol (231 mg, 1.00 mmol) in tetrahydrofuran (2.0 mL) were added diphenylfosphoryl azide (260 μL, 1.20 mmol) and 1,8-diazabicyclo[5.4.0]undes-7-ene (179 μL, 1.20 mmol). The reaction mixture was stirred for 16 hrs, diluted with toluene, and washed with water and 5% HCl. The organic layer thus obtained was dried over magnesium sulfate, filtered, and concentrated in vacuo to dryness to afford the title compound (255 mg, 100%).

$^1$H NMR (400 MHz, CDCl$_3$) δ 7.48-7.38 (m, 5H), 6.23 (s, 1H), 4.39 (s, 2H), 2.52 (d, J=7.28 Hz, 2H), 1.85-1.78 (m, 1H), 0.87 (d, J=6.60 Hz, 6H)

Example 34

(5-Isobutyl-1-phenyl-1H-pyrazol-3-yl)-N-methyl-methaneamine

Triphenylfosphine (1.6 mmol/g, 940 mg, 1.50 mmol) bound to a resin support was dissolved in tetrahydrofuran (17.5 mL), and stirred for 5. To this was added a solution of 3-(azidomethyl)-5-isobutyl-1-phenyl-1H-pyrazole (169 mg, 0.752 mmol) in tetrahydrofuran, followed by stirring for 4 hrs. Methyl iodide (141 μL, 2.26 mmol) was added to the resin, stirred for 18 hrs, and filtered. The filtered resin was washed with tetrahydrofuran and dichloromethane. The resin was added, together with potassium hydroxide (2% in MeOH, 26 mL), to methanol to give a suspension that was then stirred at 65° C. for 4 hrs, cooled to room temperature, and filtered. The filtrate was washed with dichloromethane (4~7 mL) and methanol (4~7 mL), and concentrated in vacuo. After addition of dichloromethane and 10% sodium hydrogen carbonate solution, the aqueous layer was extracted with ethyl acetate. The organic layer thus obtained was dried over magnesium sulfate, filtered, and concentrated in vacuo to dryness to afford the title compound (98.5 mg, 53.8%).

$^1$H NMR (400 MHz, CDCl$_3$) δ 7.47-7.38 (m, 5H), 6.17 (s, 1H), 3.80 (s, 2H), 2.51 (s, 3H), 2.50 (d, J=6.28 Hz, 2H), 1.88-1.79 (m, 1H), 0.85 (d, J=6.16 Hz, 6H)

Example 35

N-Methyl-N-[(5-isobutyl-1-phenyl-1H-pyrazol-3-yl)methyl]benzenesulfonamide (Compound 18)

To a solution of (5-isobutyl-1-phenyl-1H-pyrazol-3-yl)-N-methylmethaneamine (95.3 mg, 0.392 mmol) in dichloromethane (3.0 mL) was added triethylamine (60.0 μL, 0.431 mmol) at 0° C. The solution was stirred for 5 min, and added with benzenesulfonyl chloride (52.6 μL, 0.411 mmol). The temperature was elevated to room temperature at which the reaction mixture was stirred for 1 hr, added with water and an aqueous saturate sodium hydrogen carbonate solution, and then extracted with dichloromethane. The organic layer thus formed was dried over magnesium sulfate, filtered, and purified by column chromatography (Hexane:EtOAc=6:1→4:1→3:1) to afford the title compound (78.8 mg, 52.5%).

$^1$H NMR (400 MHz, CDCl$_3$) δ 7.85-7.83 (m, 2H), 7.60-7.51 (m, 3H), 7.46-7.42 (m, 2H), 7.40-7.32 (m, 3H), 6.18 (s, 1H), 4.26 (s, 2H), 2.72 (s, 3H), 2.48 (d, J=7.19 Hz, 2H), 1.83-1.76 (m, 1H), 0.85 (d, J=6.60 Hz, 6H)

$^{13}$C NMR (100 MHz, CDCl$_3$) δ 147.7, 144.6, 139.7, 137.4, 132.6, 129.1, 129.1, 128.0, 127.5, 125.6, 105.5, 47.9, 35.2, 34.6, 28.3, 22

Example 36

Ethyl 1-(4-fluorophenyl)-5-isobutyl-1H-pyrazole-3-carboxylate

To a solution of (Z)-ethyl 2-hydroxy-6-methyl-4-oxohept-2-enoate (2.01 g, 10.0 mmol) in ethanol (25 mL) was added at 0° C. 4-fluorophenyl hydrazine hydrogen chloride (1.63 g, 10.0 mmol). Thirty min. after the temperature was elevated to room temperature, 1N HCl was added to the solution that was then stirred overnight at 70° C. The solvent was removed, and water was added to the residue, followed by extraction with dichloromethane. The organic layer thus formed was dried over magnesium sulfate, filtered, and purified by column chromatography (Hexane:EtOAc=10:1→9:1→6:1) to afford the title compound (1.77 g, 60.7%).

$^1$H NMR (400 MHz, CDCl$_3$) δ 7.46-7.40 (m, 2H), 7.25-7.17 (m, 2H), 6.79 (s, 1H), 4.46 (q, J=7.14 Hz, 2H), 2.51 (d, J=7.17 Hz, 2H), 1.95-1.77 (m, 1H), 1.44 (t, J=7.14 Hz, 3H), 0.90 (d, J=6.63 Hz, 6H)

Example 37

1-(4-Fluorophenyl)-5-isobutyl-1H-pyrazole-3-carbaldehyde

Dried ethyl 1-(4-fluorophenyl)-5-isobutyl-1H-pyrazole-3-carboxylate (686 mg, 2.36 mmol) was dissolved in dichloromethane (1.8 mL), and at −78° C., diisobutylaluminum hydride (1M in hexane, 7.08 mL, 7.08 mmol) was added. After stirring for 1 hr, methanol and 3N HCl were added, and the reaction mixture was warmed to room temperature. Water was added before extraction with dichloromethane. The organic layer thus formed was dried over magnesium sulfate, filtered, and purified by column chromatography (Hexane:EtOAc=3:1) to afford the title compound (520 mg, 89.3%).

$^1$H NMR (400 MHz, CDCl$_3$) δ 10.03 (s, 1H), 7.48-7.44 (m, 2H), 7.29-7.23 (m, 2H), 6.78 (s, 1H), 2.52 (d, J=6.96 Hz, 2H), 1.94-1.80 (m, 1H), 0.92 (d, J=6.60 Hz, 6H)

Example 38

1-(4-Fluorophenyl)-3-(hydroxyamino)methyl-5-isobutylpyrazole

To a solution of hydroxylamine hydrogen chloride (221 mg, 3.18 mmol) in dichloromethane (2.2 mL) was added triethylamine (443 μL, 3.18 mmol). After stirring for 5 min, the pH of the solution was measured. A solution of 1-(4-fluorophenyl)-5-isobutyl-1H-pyrazole-3-carbaldehyde (700 mg, 2.89 mmol) in dichloromethane was added. The resulting reaction mixture was stirred for 3 hrs, added with water, and extracted with dichloromethane. The organic layer thus formed was dried over magnesium sulfate, filtered, and purified by column chromatography (Hexane:EtOAc=6:1→2:1→1:1) to afford the title compound (692 mg, 91.6%).

$^1$H NMR (300 MHz, CDCl$_3$) δ 8.24 (s, 1H), 7.44-7.40 (m, 2H), 7.24-7.19 (m, 2H), 6.56 (s, 1H), 2.52 (d, J=7.2 Hz, 2H), 1.90-1.82 (m, 1H), 0.92 (d, J=6.63 Hz, 6H)

Example 39

(1-(4-Fluorophenyl)-5-isobutyl-1H-pyrazol-3-yl)methaneamine

After being dried in vacuo, 1-(4-fluorophenyl)-3-(hydroxyamino)methyl-5-isobutylpyrazole (689 mg, 2.64 mmol) was dissolved in a mixed solvent of diethyl ether (3.0 mL) and tetrahydrofuran (2.0 mL), and lithium aluminum hydride (1M in diethyl ether, 5.80 mL, 5.80 mmol) was added at −0° C. to the solution. It was stirred for 30 min before for 30 min at room temperature. The temperature was reduced again to 0° C. to carefully add sodium sulfate hydrate to the solution. The reaction mixture was filtered through celite and sodium sulfate, concentrated in vacuo, and dried to afford the title compound (630 mg, 96.6%).

$^1$H NMR (300 MHz, CDCl$_3$) δ 7.42-7.37 (m, 2H), 7.21-7.16 (m, 2H), 6.17 (s, 1H), 3.93 (s, 2H), 2.50 (d, J=7.17 Hz, 2H), 1.89-1.80 (m, 1H), 0.91 (d, J=6.63 Hz, 6H)

Example 40

N-[(5-Isobutyl-1-(4-fluorophenyl)-1H-pyrazol-3-yl)methyl]benzenesulfonamide (Compound 20)

To a solution of (1-(4-fluorophenyl)-5-isobutyl-1H-pyrazol-3-yl)methaneamine (407 mg, 1.64 mmol) in dichloromethane (4.0 mL) was added triethylamine (252 μL, 1.81 mmol) at 0° C. The solution was stirred for 5 min, and added with benzenesulfonyl chloride (221 μL, 1.73 mmol). After the temperature was elevated to room temperature, the reaction mixture was stirred for 1 hr, added with water and an aqueous saturate sodium hydrogen carbonate solution, and extracted with dichloromethane. The organic layer thus formed was dried over magnesium sulfate, filtered, and purified by column chromatography (Hexane:EtOAc=3:1→2:1) to afford the title compound (415 mg, 82.3%).

$^1$H NMR (300 MHz, CDCl$_3$) δ 7.92-7.89 (m, 2H), 7.61-7.48 (m, 3H), 7.30-7.24 (m, 2H), 7.19-7.13 (m, 2H), 6.05 (s, 1H), 5.27 (brs, 1H), 4.21 (d, J=5.91 Hz, 2H), 2.41 (d, J=7.17 Hz, 2H), 1.83-1.71 (m, 1H), 0.85 (d, J=6.63 Hz, 6H)

$^{13}$C NMR (75 MHz, CDCl$_3$) δ 163.7, 160.4, 147.9, 144.6, 139.8, 135.7, 132.6, 129.0, 127.6, 127.5, 127.2, 116.2, 115.9, 104.9, 41.1, 35.0, 28.3, 22.4

Example 41

Ethyl 1-(tert-butyl)-5-isobutyl-1H-pyrazole-3-carboxylate

To a solution of ethyl (Z)-2-hydroxy-6-methyl-4-oxohept-2-enoate (504 mg, 2.52 mmol) in ethanol (12 mL) was slowly added tert-butylhydrazine hydrochloride (321 mg, 2.52 mmol). The solution was stirred overnight at room temperature, after TLC (Hexane:EtOAc=9:1) examination was made to see whether reaction was completed. Then, the reaction mixture was concentrated in vacuo. The concentrate was extracted with dichloromethane and water, and the organic layer thus formed was dried over magnesium sulfate, filtered, and concentrated. The concentrated filtrate was purified by column chromatography (Hexane:EtOAc=9:1) to afford the title compound (558 mg, 88%, red oil).

$^1$H NMR (300 MHz, CDCl$_3$) δ 6.59 (s, 1H), 4.39 (q, J=7.1 Hz, 2H), 2.72 (d, J=7.1 Hz, 2H), 2.12-1.99 (m, 1H), 1.71 (s, 9H), 1.42 (t, J=7.1 Hz, 3H), 1.04 (d, J=6.5 Hz, 6H).

Example 42

Ethyl 1-(4-fluorophenyl)-5-isobutyl-1H-pyrazole-3-carboxylate

To a solution of ethyl (Z)-2-hydroxy-6-methyl-4-oxohept-2-enoate (482 mg, 2.41 mmol) in ethanol (12 mL) was slowly added 4-fluorophenyl hydrazine hydrogen chloride (404 mg, 2.41 mmol). After 0.5 mL of 1M HCl was added to the solution, it was stirred overnight at room temperature. When the reaction was completed as examined by TLC (Hexane:EtOAc=6:1), the reaction mixture was concentrated in vacuo. The concentrate was extracted with dichloromethane and water, and the organic layer thus formed was dried over anhydrous magnesium sulfate, filtered, and concentrated. The concentrated filtrate was purified by column chromatography (Hexane:EtOAc=12:1) to afford the title compound (387 mg, 55%, red oil).

$^1$H NMR (300 MHz, CDCl$_3$) δ 7.45-7.41 (m, 2H), 7.25-7.18 (m, 2H), 4.46 (q, J=7.1 Hz, 2H), 2.51 (d, J=7.2 Hz, 2H), 1.90-1.81 (m, 1H), 1.44 (t, J=7.1 Hz, 3H), 0.91 (d, J=6.6 Hz, 6H)

Example 43

1-(4-Fluorophenyl)-5-isobutyl-1H-pyrazole-3-carbaldehyde

To a solution of ethyl 1-(4-fluorophenyl)-5-isobutyl-1H-pyrazole-3-carboxylate (1.01 g, 3.46 mmol) in dichloromethane (10 mL) was added dropwise at −78° C. diisobutylaluminum hydride (10.4 mL, 10.4 mmol, 1.0M in toluene), followed by stirring for 1 hr. When the reaction was completed as measured by TLC, the reaction mixture was acidified with 3.0M HCl to a pH of 2~3. The reaction mixture was extracted with dichloromethane, and the extract was dried over anhydrous sodium sulfate, filtered, and concentrated. The concentrated filtrate was purified by column chromatography (Hexane:EtOAc=10:1) to afford the title compound (501 mg, 59%, yellow solid).

$^1$H NMR (300 MHz, CDCl$_3$) δ 10.03 (s, 1H), 7.48-7.44 (m, 2H), 7.30-7.23 (m, 2H), 6.77 (s, 2H), 2.54 (d, J=7.2 Hz, 2H), 1.94-1.80 (m, 1H), 0.92 (d, J=6.6 Hz, 6H).

Example 44

1-(4-Fluorophenyl)-5-isobutyl-1H-pyrazole-3-carbaldehyde oxime

To a solution of hydroxylamine hydrogen chloride (161 mg, 2.32 mmol) in dichloromethane (5 mL) was slowly added at 0° C. drops of triethylamine (0.33 mL, 2.32 mmol), followed by the slow addition of drops of a solution of 1-(4-fluorophenyl)-5-isobutyl-1H-pyrazole-3-carbaldehyde (501 mg, 2.03 mmol) I dichloromethane (2 mL). The reaction mixture was stirred at room temperature for 4 hrs, and the progression of the reaction was monitored by TLC. After extraction with dichloromethane and water, the organic layer thus formed was dried over anhydrous sodium sulfate, filtered, and concentrated to afford the title compound (487 mg, crude, yellow solid).

¹H NMR (300 MHz, CDCl₃) δ 8.24 (s, 1H), 7.44-7.40 (m, 2H), 7.24-7.19 (m, 2H), 6.56 (s, 1H), 2.52 (d, J=7.2 Hz, 2H), 1.90-1.82 (m, 1H), 0.92 (d, J=6.63 Hz, 6H)

Example 45

{1-(4-Fluorophenyl)-5-isobutyl-1H-pyrazol-3-yl}methaneamine

To a solution of 1-(4-fluorophenyl)-5-isobutyl-1H-pyrazole-3-carbaldehyde oxime (487 mg, 1.86 mmol) in diethyl ether/tetrahydrofuran (3/10 mL) was added dropwise a lithium aluminium hydride solution (0.62 mL, 0.615 mmol, 1.0 M in diethyl ether) at 0° C. Thirty minutes after the addition, the reaction mixture was stirred overnight at room temperature. When the reaction was completed as measured by TLC (Hexane:EtOAc=2:1), drops of Na₂SO₄.10H₂O were slowly added at 0° C. Then, the reaction mixture was filtered at a reduced pressure through celite, and the filtrate was concentrated to afford the title compound (422 mg, 92%, yellow oil) without further purification.

¹H NMR (300 MHz, CDCl₃) δ 7.42-7.38 (m, 2H), 7.18 (t, J=8.5 Hz, 2H), 6.17 (s, 1H), 3.94 (s, 2H), 2.50 (d, J=7.1 Hz, 2H), 1.89-1.80 (m, 1H), 1.55 (brs, 2H), 0.91 (d, J=6.6 Hz, 6H)

Example 46

N-[{1-(4-Fluorophenyl)-5-isobutyl-1H-pyrazol-3-yl}methyl]quinoline-8-sulfonamide (Compound 21)

To a solution of {1-(4-fluorophenyl)-5-isobutyl-1H-pyrazol-3-yl}methaneamine (211 mg, 0.853 mmol) in dichloromethane (6 mL) was added dropwise at 0° C. triethylamine (0.13 mL, 0.939 mmol), followed by the addition of drops of quinoline-8-sulfonyl chloride (213 mg, 0.896 mmol). At room temperature, the reaction mixture was stirred for 4 hrs. When the reaction was completed as measured by TLC, extraction was made with dichloromethane and water. The organic layer thus formed was dried over anhydrous sodium sulfate, filtered, concentrated, and purified by column chromatography (Hexane:EtOAc=2:1→1:1) to afford the title compound (317 mg, 85%, white solid).

¹H NMR (300 MHz, CDCl₃) δ 8.99 (dd, J=4.2 Hz, 1.7 Hz, 1H), 8.47 (dd, J=7.3 Hz, 1.3 Hz, 1H), 8.26 (dd, J=8.3 Hz, 1.7 Hz, 1H), 8.04 (dd, J=8.2 Hz, 1.3 Hz, 1H), 7.65 (t, J=7.7 Hz, 1H), 7.52 (dd, J=8.3 Hz, 4.1 Hz, 1H), 7.11 (d, J=6.6 Hz, 4H), 6.82 (t, J=6.3 Hz, 1H), 5.99 (s, 1H), 4.20 (d, J=6.4 Hz, 2H), 2.31 (d, J=7.1 Hz, 2H), 1.77-1.60 (m, 1H), 0.80 (d, J=6.6 Hz, 6H)

¹³C NMR (75 MHz, CDCl₃) δ 163.6, 160.3, 151.1, 148.4, 143.9, 143.4, 136.8, 136.4, 135.7, 133.1, 131.0, 128.9, 127.4, 127.3, 125.6, 122.1, 116.0, 115.7, 105.2, 41.6, 34.9, 28.3, 22.3

Example 47

Ethyl 1-(tert-butyl)-5-phenyl-1H-pyrazole-3-carboxylate

To a solution of ethyl (Z)-2-hydroxy-4-oxo-4-phenylbut-2-enoate (86.3 mg, 0.392 mmol) in ethanol (2.5 mL) was slowly added tert-butyl hydrazine hydrogen chloride (50.1 mg, 0.392 mmol). The solution was stirred overnight at room temperature. When the reaction was completed as measured by TLC (Hexane:EtOAc=6:1), the reaction mixture was concentrated in vacuo. After the extraction of the concentrate with dichloromethane and water, the organic layer thus formed was dried over anhydrous sodium sulfate, filtered, concentrated, and purified by column chromatography (Hexane:EtOAc=15:1→6:1) to afford the title compound (59.8 mg, 86%, white solid).

¹H NMR (300 MHz, CDCl₃) δ 7.47-7.36 (m, 5H), 6.71 (s, 1H), 4.43 (q, J=7.1 Hz, 2H), 1.54 (s, 9H), 1.43 (t, J=7.1 Hz, 3H)

Example 48

Ethyl 5-phenyl-1H-pyrazole-3-carboxylate

To a solution of ethyl (Z)-2-hydroxy-4-oxo-4-phenylbut-2-enoate (1.02 g, 4.64 mmol) in ethanol (5 mL) was slowly added hydrazine monohydrate (0.29 mL, 4.64 mmol), followed by the addition of 1M HCl 0.3 mL. The reaction mixture was stirred overnight at room temperature. After the reaction was completed as monitored by TLC (Hexane:EtOAc=4:1), concentration in vacuo was conducted. The concentrate was extracted with dichloromethane and water, the organic layer thus formed was dried over anhydrous magnesium sulfate, filtered, and concentrated. The concentrated filtrate was recrystallized in dichloromethane and purified by column chromatography (dichloromethane:MeOH=15:1) to afford the title compound (843 mg, 84%, yellow solid).

¹H NMR (300 MHz, CDCl₃) δ 11.25 (brs, 1H), 7.80 (d, J=7.1 Hz, 2H), 7.50-7.38 (m, 3H), 7.16 (s, 1H), 4.45 (q, J=7.1 Hz, 2H), 1.45 (t, J=7.1 Hz, 3H)

Example 49

Ethyl 1-isobutyl-5-phenyl-1H-pyrazole-3-carboxylate

To a solution of ethyl 5-phenyl-1H-pyrazole-3-carboxylate (660 mg, 3.05 mmol) in N,N-dimethylformamide (10.2 mL) was added potassium carbonate (4.22 g, 30.5 mmol) at 0° C., followed by stirring for 1 hr. Again, drops of 1-iodo-2-methylpropane (1.77 g, 9.15 mmol) were added, and stirring was conducted overnight at room temperature. When the reaction was completed as monitored by TLC, water was added to the reaction mixture at 0° C. before extraction with ethyl acetate and brine. The organic layer thus formed was dried over anhydrous magnesium sulfate, filtered, concentrated, and purified by column chromatography (Hexane:EtOAc=9:1→1:1) to afford the title compound (62.2 mg, 7.5%, yellow oil).

¹H NMR (300 MHz, CDCl₃) δ 7.52-7.47 (m, 3H), 7.42-7.39 (m, 2H), 6.83 (s, 1H), 4.46 (q, J=7.2 Hz, 2H), 4.04 (d, J=7.6 Hz, 2H), 2.41-2.20 (m, 1H), 1.44 (t, J=7.2 Hz, 3H), 0.78 (d, J=6.8 Hz, 6H)

Example 50

1-(tert-Butyl)-5-phenyl-1H-pyrazole-3-carbaldehyde

To a solution of ethyl 1-(tert-butyl)-5-phenyl-1H-pyrazole-3-carboxylate (247 mg, 1.07 mmol) in dichloromethane (6 mL) was added Dess-Martin periodinane (518 mg, 1.22 mmol) at room temperature, followed by stirring for 2 hrs at the same temperature. When the reaction was completed as monitored by TLC (Hexane:EtOAc=4:1), extraction with dichloromethane and water was made. The organic layer was dried over anhydrous sodium sulfate, filtered, and concentrated. The concentrated filtrate was purified by column chromatography (Hexane:EtOAc=4:1→CH$_2$Cl$_2$) to afford the title compound (226 mg, 92%, white solid).

$^1$H NMR (300 MHz, CDCl$_3$) δ 10.03 (s, 1H), 7.49-7.42 (m, 3H), 7.39-7.36 (m, 2H), 6.72 (s, 1H), 1.54 (s, 9H)

Example 51

1-(tert-Butyl)-5-phenyl-1H-pyrazole-3-carbaldehyde oxime

To a solution of hydroxylamine hydrogen chloride (84.2 mg, 1.21 mmol) in dichloromethane (6 mL) were slowly added drops of triethylamine (0.17 mL, 1.21 mmol) at 0° C., followed by the slow addition of drops of a solution of 1-(tert-butyl)-5-phenyl-1H-pyrazole-3-carbaldehyde (226 mg, 0.990 mmol) in dichloromethane (2 mL). After stirring at room temperature for 4 hrs, the reaction progression was monitored by TLC (Hexane:EtOAc=1:1). When the reaction completed, the reaction mixture was extracted with dichloromethane and brine, and the organic layer thus formed was dried over anhydrous magnesium sulfate, filtered, and concentrated to afford the title compound (93.5 mg, crude, yellow oil).

$^1$H NMR (300 MHz, CDCl$_3$) δ 8.22 (s, 1H), 7.51-7.40 (m, 5H), 7.21 (brs, 1H), 6.53 (s, 1H), 2.52 (d, J=7.16 Hz, 2H), 1.88-1.80 (m, 1H), 0.88 (d, J=6.60 Hz, 6H)

Example 52

{1-(tert-Butyl)-5-phenyl-1H-pyrazol-3-yl}methaneamine

To a solution of 1-(tert-butyl)-5-phenyl-1H-pyrazole-3-carbaldehyde oxime (93.5 mg, 0.384 mmol) in tetrahydrofuran (5 mL) was added dropwise a lithium aluminum hydride solution (0.62 mL, 0.615 mmol, 1.0 M in diethyl ether) at 0° C. The resulting solution was stirred for 30 min at the temperature before overnight at room temperature. When the reaction was completed as measured by TLC (Hexane:EtOAc=1:1), drops of Na$_2$SO$_4$.10H$_2$O were slowly added at 0° C. The reaction mixture was filtered through celite, and the filtrate was concentrated. The concentrate was purified by column chromatography (Hexane:EtOAc=3:1→Hexane:EtOAc=1:1→CH$_2$Cl$_2$:MeOH=10:1) to afford the title compound (71.0 mg, 81%, yellow oil).

$^1$H NMR (300 MHz, CDCl$_3$) δ 7.43-7.37 (m, 5H), 6.10 (s, 1H), 3.93 (s, 2H), 2.06 (brs, 2H), 1.48 (s, 9H)

Example 53

N-[{1-(tert-Butyl)-5-phenyl-1H-pyrazol-3-yl}methyl]benzenesulfonamide (Compound 23)

To a solution of {1-(tert-butyl)-5-phenyl-1H-pyrazol-3-yl}methaneamine (71.0 mg, 0.310 mmol) in dichloromethane (2.5 mL) was added dropwise at triethylamine 0° C. (0.05 mL, 0.341 mmol), followed by the addition of drops of benzenesulfonyl chloride (0.042 mL, 0.325 mmol). The reaction mixture was stirred at room temperature for 3 hrs, and when the reaction was completed as measured by TLC, water was added dropwise. After extraction with dichloromethane and water, the organic layer thus formed was dried over anhydrous sodium sulfate, filtered, concentrated, and purified by column chromatography (Hexane:EtOAc=3:1) to afford the title compound (90.3 mg, 79%, white solid).

$^1$H NMR (300 MHz, CDCl$_3$) δ 7.98-7.92 (m, 2H), 7.60-7.50 (m, 3H), 7.43-7.37 (m, 3H), 7.30-7.26 (m, 2H), 5.94 (s, 1H), 5.18 (t, J=5.5 Hz, 1H), 4.23 (d, J=5.5 Hz, 2H), 1.40 (s, 9H)

$^{13}$C NMR (300 MHz, CDCl$_3$) δ 143.9, 140.0, 133.8, 132.5, 130.3, 129.0, 128.5, 127.8, 127.3, 107.6, 61.3, 41.2, 31.1

Example 54

Ethyl 4-(4-fluorophenyl)-2,4-dioxobutanoate

To a solution of sodium metal (1.03 g, 45.0 mmol) in ethanol (100 mL) were slowly added drops of 1-(4-fluorophenyl)ethanone (4.50 mL, 36.9 mmol) at 0° C. The solution was stirred for 30 min, and then slowly added drops of diethyl oxalate (5.50 mL, 40.5 mmol) at the same temperature. Following stirring overnight at room temperature, the progression of the reaction was monitored by TLC (Hexane:EtOAc=4:1). When the reaction was completed, the reaction mixture was concentrated in vacuo. To the concentrate, 6M HCl was added dropwise at 0° C., followed by extraction with dichloromethane and water. The organic layer thus formed was dried over anhydrous magnesium sulfate, filtered, and concentrated to afford the title compound without further purification (9.07 g, quant., yellow solid).

$^1$H NMR (300 MHz, CDCl$_3$) δ 8.09-8.04 (m, 2H), 7.24-7.20 (m, 2H), 7.07 (s, 1H), 4.44 (q, J=7.2 Hz, 2H), 1.45 (t, J=7.2 Hz, 3H)

Example 55

Ethyl 1-(tert-butyl)-5-(4-fluorophenyl)-1H-pyrazole-3-carboxylate

To a solution of ethyl 4-(4-fluorophenyl)-2,4-dioxobutanoate (55.9 mg, 0.235 mmol) in ethanol (2.5 mL) was slowly added tert-butyl hydrazine hydrogen chloride (48.0 mg, 0.378 mmol). Following the addition of 1M HCl 0.5 mL thereto, the reaction mixture was stirred overnight at room temperature. When the reaction was completed as monitored by TLC (Hexane:EtOAc=6:1), the reaction mixture was concentrated in vacuo. After extraction with dichloromethane and water, the organic layer thus formed was dried over anhydrous magnesium sulfate, filtered, and concentrated. The concentrated filtrate was purified by column chromatography (Hexane:EtOAc=6:1) to afford the title compound (59.1 mg, 87%, yellow solid).

$^1$H NMR (300 MHz, CDCl$_3$) δ 7.38-7.32 (m, 2H), 7.17-7.11 (m, 2H), 6.71 (s, 1H), 4.43 (q, J=7.1 Hz, 2H), 1.53 (s, 9H), 1.43 (t, J=7.1 Hz, 3H)

Example 56

Ethyl 5-(4-fluorophenyl)-1H-pyrazole-3-carboxylate

To a solution of ethyl 4-(4-fluorophenyl)-2,4-dioxobutanoate (512 mg, 2.15 mmol) in ethanol (7 mL) was slowly added hydrazine monohydrate (0.14 mL, 2.15 mmol). Following the addition of 1M HCl 0.1 mL thereto, the reaction mixture was stirred overnight at room temperature. When the reaction was completed as monitored by TLC (Hexane:EtOAc=4:1), the reaction mixture was concentrated in vacuo. After extraction with dichloromethane and water, the organic layer thus formed was dried over anhydrous magnesium sulfate, filtered, and concentrated. The concentrated filtrate was recrystallized in dichloromethane, and purified by column chromatography (Hexane:EtOAc=4:1→CH$_2$Cl$_2$:MeOH=12:1) to afford the title compound (290 mg, 58%, yellow solid).

$^1$H NMR (300 MHz, CDCl$_3$) δ 7.78 (brs, 2H), 7.18-7.14 (m, 2H), 7.11 (s, 1H), 4.46 (q, J=7.0, 2H), 1.45 (t, J=7.0 Hz, 3H)

Example 57

Ethyl 5-(4-fluorophenyl)-1-isobutyl-1H-pyrazole-3-carboxylate

To a solution of ethyl 5-(4-fluorophenyl)-1H-pyrazole-3-carboxylate (290 mg, 1.24 mmol) in N,N-dimethylformamide (7 mL) was added potassium carbonate (1.77 g, 12.4 mmol) at 0° C., followed by stirring for one hour. Again, the solution was added with drops of 1-iodo-2-methylpropane (716 mg, 3.71 mmol), and stirred at room temperature for 3 hrs. When the reaction was completed as monitored by TLC, the reaction mixture was added water at 0° C., and extracted with ethyl acetate and brine. The organic layer thus formed was dried over anhydrous magnesium sulfate, filtered, concentrated, and purified by column chromatography (Hexane:EtOAc=10:1→4:1) to afford the title compound. (22.4 mg, 6.2%, yellow oil).

$^1$H NMR (400 MHz, CDCl$_3$) δ 7.39-7.35 (m, 2H), 7.22-7.17 (m, 2H), 6.81 (s, 1H), 4.45 (q, J=7.0 Hz, 2H), 3.99 (d, J=7.6 Hz, 2H), 2.30-2.19 (m, 1H), 1.43 (t, J=7.0 Hz, 3H), 0.77 (d, J=6.8 Hz, 6H)

Example 58

1-(tert-Butyl)-5-(4-fluorophenyl)-1H-pyrazole-3-carbaldehyde

To a solution of ethyl 1-(tert-butyl)-5-(4-fluorophenyl)-1H-pyrazole-3-carboxylate (234 mg, 0.940 mmol) in dichloromethane (6 mL) was added Dess-Martin periodinane (467 mg, 1.10 mmol) at room temperature, followed by stirring for 2 hrs at the same temperature. When the reaction was completed as monitored by TLC (Hexane:EtOAc=4:1), extraction was carried out with dichloromethane and water. The organic layer thus formed was dried over anhydrous sodium sulfate, filtered, and concentrated. The concentrated filtrate was purified by column chromatography (Hexane:EtOAc=4:1→CH$_2$Cl$_2$) to afford the title compound (210 mg, 91%, white solid).

$^1$H NMR (300 MHz, CDCl$_3$) δ 10.01 (s, 1H), 7.38-7.33 (m, 2H), 7.15 (t, J=8.2 Hz, 2H), 6.71 (s, 1H), 1.54 (s, 9H)

Example 59

1-(tert-Butyl)-5-(4-fluorophenyl)-1H-pyrazole-3-carbaldehyde oxime

To a solution of hydroxylamine hydrogen chloride (81.8 mg, 1.18 mmol) in dichloromethane (6 mL) was slowly added drops of triethylamine (0.17 mL, 1.18 mmol) at 0° C., followed by the slow addition of drops of a solution of 1-(tert-butyl)-5-(4-fluorophenyl)-1H-pyrazole-3-carbaldehyde (210 mg, 0.852 mmol) in dichloromethane (2 mL). After stirring at room temperature for 4 hrs, the reaction progression was monitored by TLC (Hexane:EtOAc=1:1). The reaction mixture was extracted with dichloromethane and brine, and the organic layer was dried over anhydrous magnesium sulfate, filtered, and concentrated to afford the title compound without further purification (97.8 mg, crude, yellow oil).

$^1$H NMR (300 MHz, CDCl$_3$) δ 9.75 (s, 1H), 8.15-8.01 (m, 2H), 7.30-7.24 (m, 2H), 6.81 (s, 1H), 1.35 (s, 9H)

Example 60

{1-(tert-Butyl)-5-(4-fluorophenyl)-1H-pyrazol-3-yl}methaneamine

To a solution of 1-(tert-butyl)-5-(4-fluorophenyl)-1H-pyrazole-3-carbaldehyde oxime (97.8 mg, 0.374 mmol) in tetrahydrofuran (5 mL) was added a lithium aluminum hydride solution (0.83 mL, 0.824 mmol, 1.0 M in diethyl ether) at 0° C. The resulting solution was stirred for 30 min at the temperature before overnight at room temperature. When the reaction was completed as measured by TLC (Hexane:EtOAc=1:1), drops of Na$_2$SO$_4$.10H$_2$O were slowly added at 0° C. The reaction mixture was filtered through celite in vacuo, and the filtrate was concentrated. The concentrate was purified by column chromatography (Hexane:EtOAc=1:1→CH$_2$Cl$_2$:MeOH=10:1) to afford the title compound. (72.6 mg, 78%, yellow oil).

$^1$H NMR (300 MHz, CDCl$_3$) δ 7.43-7.32 (m, 2H), 7.11 (t, J=8.7 Hz, 2H), 6.09 (s, 1H), 3.92 (s, 2H), 1.90 (brs, 2H), 1.47 (s, 9H)

Example 61

N-[{1-(tert-Butyl)-5-(4-fluorophenyl)-1H-pyrazol-3-yl}methyl]benzenesulfonamide (Compound 22)

To a solution of {1-(tert-butyl)-5-(4-fluorophenyl)-1H-pyrazol-3-yl}methaneamine (72.6 mg, 0.294 mmol) in dichloromethane (2.5 mL) was added dropwise triethylamine (0.05 mL, 0.323 mmol) at 0° C., followed by the addition of drops of benzenesulfonyl chloride (0.04 mL, 0.308 mmol). The reaction mixture was stirred for 3 hrs at room temperature. When the reaction was completed as measured by TLC, water was added. After extraction with dichloromethane and water, the organic layer was dried over anhydrous sodium sulfate, filtered, concentrated, and purified by column chromatography (Hexane:EtOAc=3:1) to afford the title compound (92.9 mg, 82%, white solid).

$^1$H NMR (300 MHz, CDCl$_3$) δ 7.96-7.93 (m, 2H), 7.63-7.51 (m, 3H), 7.42-7.35 (m, 1H), 7.29-7.23 (m, 2H), 7.10 (t, J=8.7 Hz, 1H), 5.94 (s, 1H), 5.08 (brs, 1H), 4.24-4.21 (m, 2H), 1.40 (s, 9H)

$^{13}$C NMR (100 MHz, CDCl$_3$) δ 164.0, 161.6, 144.0, 143.9, 142.7, 140.0, 133.8, 132.5, 132.0, 132.0, 130.3, 129.7, 129.7, 129.0, 128.5, 127.8, 127.3, 115.0, 114.8, 107.9, 107.6, 61.3, 41.2, 31.1

Example 62

Ethyl 2,4-dioxo-4-{4-(trifluoromethyl)phenyl}butanoate

To a solution of sodium metal (239 mg, 10.4 mmol) in ethanol (17 mL) were slowly added drops of 1-{4-(trifluoromethyl)phenyl}ethanone (949 mg, 4.94 mmol) at 0° C. Thirty minutes later, drops of diethyl oxalate (0.70 mL, 5.19 mmol) were slowly added at the same temperature. Stirring was conducted overnight at room temperature, and when the reaction was completed as measured by TLC (Hexane:EtOAc=1:1), the reaction mixture was concentrated in vacuo. At 0° C., 3M HCl was added to the concentrate, followed by extraction with dichloromethane and water. The organic layer thus formed was dried over anhydrous magnesium sulfate, filtered, and concentrated to afford the title compound without further purification (1.30 g, 91%, crude yellow solid).

$^1$H NMR (300 MHz, CDCl$_3$) δ 8.14 (d, J=8.2 Hz, 2H), 7.84-7.79 (m, 2H), 7.13 (s, 1H), 4.46 (q, J=7.2 Hz, 2H), 1.47 (t, J=7.2 Hz, 3H)

Example 63

Ethyl 1-(tert-butyl)-5-{4-(trifluoromethyl)phenyl}-1H-pyrazole-3-carboxylate

To a solution of ethyl 2,4-dioxo-4-{4-(trifluoromethyl) phenyl}butanoate (155 mg, 0.536 mmol) in ethanol (3 mL) was slowly added tert-butyl hydrazine hydrogen chloride (69.2 mg, 0.536 mmol), followed by the addition of 1M HCl 0.5 mL. The reaction mixture was stirred overnight at room temperature. When the reaction was completed as measured by TLC (Hexane:EtOAc=6:1), the reaction mixture was concentrated in vacuo. After extraction with dichloromethane and water, the organic layer thus formed was dried over anhydrous magnesium sulfate, filtered, and concentrated. The concentrate was purified by column chromatography (Hexane:EtOAc=10:1→6:1) to afford the title compound (136 mg, 75%, yellow solid).

$^1$H NMR (300 MHz, CDCl$_3$) δ 7.72 (d, J=8.0 Hz, 2H), 7.52 (d, J=8.0 Hz, 2H), 6.73 (s, 1H), 4.44 (q, J=7.1 Hz, 2H), 1.54 (s, 9H), 1.43 (t, J=7.1 Hz, 3H)

Example 64

Ethyl 2,4-dioxo-4-{4-(piperidin-1-yl) phenyl}butanoate

To a solution of sodium metal (Na; 1.12 g, 48.7 mmol) in ethanol (100 mL) were slowly added drops of 1-{4-(piperidin-1-yl)phenyl}ethanone (6.52 g, 32.1 mmol) at 0° C. Thirty minutes later, diethyl oxalate (4.78 mL, 35.3 mmol) was slowly added at the same temperature. Stirring was conducted overnight at room temperature, and when the reaction was completed as measured by TLC (Hexane: EtOAc=4:1), the reaction mixture was concentrated in vacuo. At 0° C., 6 M HCl was added to the concentrate, followed by extraction with dichloromethane and water. The organic layer thus formed was dried over anhydrous magnesium sulfate, filtered, and concentrated to afford the title compound without further purification (9.34 g, 92%, crude, yellow solid).

$^1$H NMR (300 MHz, CDCl$_3$) δ 7.94 (d, J=9.0 Hz, 2H), 7.30 (s, 1H), 6.92 (d, J=9.0 Hz, 2H), 4.43 (q, J=7.1 Hz, 2H), 3.47 (brs, 4H), 1.72 (brs, s, 6H), 1.47 (t, J=7.1 Hz, 3H)

Example 65

Ethyl 1-(tert-butyl)-5-{4-(piperidin-1-yl)phenyl}-1H-pyrazole-3-carboxylate

To a solution of ethyl 2,4-dioxo-4-{4-(piperidin-1-yl) phenyl}butanoate (426 mg, 1.41 mmol) in a mixed solvent of ethanol (10 mL) and dichloromethane (2 mL) was slowly added tert-butyl hydrazine hydrogen chloride (217 mg, 1.70 mmol), followed by the addition of 0.5 mL of 1 M HCl. The reaction mixture was stirred at room temperature for a day and then refluxed for another day with stirring. When the reaction mixture was completed as measured by TLC (Hexane:EtOAc=4:1), concentration was made in vacuo. After extraction with dichloromethane and water, the organic layer thus formed was dried over anhydrous magnesium sulfate, filtered, and concentrated. The concentrate was purified by column chromatography (Hexane:EtOAc=10:1) to afford the title compound (469 mg, 75%, crude yellow solid).

$^1$H NMR (300 MHz, CDCl$_3$) δ 7.71 (d, J=8.7 Hz, 2H), 6.95 (d, J=8.7 Hz, 2H), 6.68 (s, 1H), 4.42 (q, J=7.1 Hz, 2H), 3.29-3.26 (m, 4H), 1.80-1.68 (m, 6H), 1.42 (t, J=7.1 Hz, 3H)

Example 66

Ethyl 4-(4-cyclohexylphenyl)-2,4-dioxobutanoate

To a solution of sodium metal (1.03 g, 45.0 mmol) in ethanol (120 mL) were slowly added drops of 1-(4-cyclohexylphenyl)ethanone (6.14 g, 30.0 mmol) at 0° C. Thirty minutes later, drops of diethyl oxalate (4.50 mL, 33.0 mmol) were slowly added at the same temperature. Stirring was conducted overnight at room temperature, and when the reaction was completed as measured by TLC (Hexane: EtOAc=4:1), the reaction mixture was concentrated in vacuo. At 0° C., 6 M HCl was added to the concentrate, followed by extraction with dichloromethane and water. The organic layer thus formed was dried over anhydrous magnesium sulfate, filtered, and concentrated to afford the title compound without further purification (9.17 g, 67%, crude yellow solid).

$^1$H NMR (300 MHz, CDCl$_3$) δ 7.97 (d, J=8.3 Hz, 2H), 7.38 (d, J=8.3 Hz, 2H), 7.11 (s, 1H), 4.44 (q, J=7.1 Hz, 2H), 2.62 (brs, s, 2H), 1.90 (brs, s, 4H), 1.50 (m, 8H)

Example 67

Ethyl 1-(tert-butyl)-5-(4-cyclohexylphenyl)-1H-pyrazole-3-carboxylate

To a solution of ethyl 4-(4-cyclohexylphenyl)-2,4-dioxobutanoate (304 mg, 1.01 mmol) in a mixed solvent of ethanol (5 mL) and dichloromethane (1 mL) was slowly added tert-butyl hydrazine hydrogen chloride (161 mg, 1.29 mmol), followed by the addition of 0.5 mL of 1M HCl. The reaction mixture was stirred at room temperature for a day and then refluxed for another day with stirring. When the reaction mixture was completed as measured by TLC (Hexane:EtOAc=4:1), concentration was made in vacuo. After extraction with dichloromethane and water, the organic layer thus formed was dried over anhydrous magnesium sulfate, filtered, and concentrated. The concentrate was purified by column chromatography (Hexane:EtOAc=10:1→4:1→CH$_2$Cl$_2$) to afford the title compound. (309 mg, 87%, yellow solid).

$^1$H NMR (300 MHz, CDCl$_3$) δ 7.27 (s, 4H), 6.70 (s, 1H), 4.42 (q, J=7.1 Hz, 2H), 2.63-2.55 (m, 1H), 1.97-1.79 (m, 5H), 1.53 (s, 9H), 1.47-1.31 (m, 8H)

Example 68

Sodium naphthalen-2-ylmethane sulfonate

To a suspension of 2-(bromomethyl)naphthalene (2.00 g, 8.69 mmol) in water (12 mL) was added sodium sulfite (1.89 g, 9.24 mmol) at room temperature, followed by refluxing for a day at room temperature. When the reaction was completed as measured by TLC, the reaction mixture was filtered, and the filtrate was concentrated to afford 1.64 g of the title compound.

Example 69

Naphthalen-2-ylmethanesulfonyl chloride

To a solution of sodium naphthalen-2-ylmethane sulfonate (855 mg, 3.50 mmol) in $CH_2Cl_2$/DMF (4 mL/1 mL) was slowly added thionyl chloride (1.00 mL, 13.8 mmol), followed by stirring at room temperature for a day. When the reaction was completed as measured by TLC (Hexane:EtOAc=6:1), the reaction mixture was concentrated in vacuo. Sodium hydrogen carbonate was added to the concentrated and stirred for 30 min. After extraction with dichloromethane and water, the organic layer thus formed was dried over anhydrous sodium sulfate, filtered, and concentrated to afford the title compound (129 mg, crude, white solid).

Example 70

Ethyl 5-isobutyl-1-phenyl-1H-pyrazole-3-carboxylate

To a solution of (Z)-ethyl 2-hydroxy-6-methyl-4-oxohept-2-enoate (1.34 g, 6.68 mmol) in ethanol (10 mL) was slowly added phenyl hydrazine (0.66 mL, 6.68 mmol) at room temperature, followed by stirring for a day. When the reaction was completed as measured by TLC (Hexane:EtOAc=6:1), the reaction mixture was concentrated in vacuo. After extraction with dichloromethane and water, the organic layer thus formed was dried over anhydrous sodium sulfate, filtered, and concentrated. The concentrate was purified by column chromatography (Hexane:EtOAc=6:1) to afford the title compound (1.45 g, 80%, red oil).

$^1$H NMR (300 MHz, $CDCl_3$) δ 7.55-7.31 (m, 5H), 6.79 (s, 1H), 4.46 (q, J=7.1 Hz, 2H), 2.55 (d, J=7.2 Hz, 2H), 1.91-1.82 (m, 1H), 1.44 (t, J=7.1 Hz, 3H), 0.90 (d, J=6.6 Hz, 6H)

Example 71

5-Isobutyl-1-phenyl-1H-pyrazole-3-carbaldehyde

To a solution of ethyl 5-isobutyl-1-phenyl-1H-pyrazole-3-carboxylate (1.45 g, 5.31 mmol) in dichloromethane (4 mL) was added dropwise diisobutylaluminum hydride (15.9 mL, 15.9 mmol, 1.0M in hexane) at −78° C., followed by stirring for 50 min. When the reaction was completed as measured by TLC, the reaction mixture was acidified to a pH of 2~3 with 3.0M HCl. After extraction with dichloromethane, the extract was dried over anhydrous sodium sulfate, filtered, and concentrated. The concentrate was purified by column chromatography (Hexane:EtOAc=6:1→1:1) to afford the title compound (860 mg, 71%, pale yellow oil).

$^1$H NMR (300 MHz, $CDCl_3$) δ 10.0 (s, 1H), 7.61-7.46 (m, 5H), 6.78 (s, 1H), 2.58 (d, J=7.2 Hz, 2H), 1.93-1.81 (m, 1H), 0.91 (d, J=6.6 Hz, 6H)

Example 72

5-Isobutyl-1-phenyl-1H-pyrazole-3-carbaldehyde oxime

To a solution of hydroxylamine hydrogen chloride (335 mg, 4.82 mmol) in dichloromethane (4 mL) were slowly added drops of triethylamine (0.33 mL, 2.32 mmol) at 0° C., followed by the slow addition of drops of a solution of dichloromethane (2 mL) in 5-isobutyl-1-phenyl-1H-pyrazole-3-carbaldehyde (1.00 g, 4.38 mmol). The reaction mixture was stirred at room temperature for 1 hr. When the reaction was completed as measured by TLC, the reaction mixture was extracted with dichloromethane and water. The organic layer thus formed was dried over anhydrous sodium sulfate, filtered, and concentrated to afford the title compound (1.03 g, crude, yellow oil).

$^1$H NMR (300 MHz, $CDCl_3$) δ 7.97-8.01 (m, 2H), 7.94 (d, 1H), 7.55-7.58 (m, 2H), 7.46 (s, 1H), 7.14 (d, 1H), 4.75 (s, 2H)

Example 73

(5-Isobutyl-1-phenyl-1H-pyrazol-3-yl)methaneamine

To a solution of 5-isobutyl-1-phenyl-1H-pyrazole-3-carbaldehyde oxime (1.03 g, 4.22 mmol) in diethyl ether/tetrahydrofuran (5 mL/2 mL) was added dropwise a lithium aluminum hydride solution (9.29 mL, 9.29 mmol, 1.0 M in diethyl ether) at 0° C. The resulting solution was stirred for 30 min at the temperature and then at room temperature for one hour. When the reaction was completed as measured by TLC (Hexane:EtOAc=3:1), drops of $Na_2SO_4.10H_2O$ were slowly added to the reaction mixture at 0° C. It was filtered through celite in vacuo, and filtered. The filtrate was concentrated to afford the title compound without further purification (611 mg, 63%, yellow oil).

$^1$H NMR (300 MHz, $CDCl_3$) δ 7.52-7.30 (m, 5H), 6.18 (s, 1H), 3.95 (s, 2H), 2.54 (d, J=7.2 Hz, 2H), 1.90-1.79 (m, 3H), 0.90 (d, J=6.6 Hz, 6H)

Example 74

N-[(5-Isobutyl-1-phenyl-1H-pyrazol-3-yl)methyl]-1-(naphthalen-2-yl)methanesulfonamide (Compound 24)

To a solution of naphthalen-2-ylmethanesulfonyl chloride (581 mg, 2.41 mmol) in dichloromethane (3 mL) was added an aqueous saturate sodium hydrogen carbonate solution (3 mL), followed by the slow addition of drops of (5-isobutyl-1-phenyl-1H-pyrazol-3-yl)methaneamine (72.3 mg, 0.318 mmol) at 0° C. Triethylamine (0.05 mL, 0.349 mmol) was added at the same temperature before stirring for 2 hrs at room temperature. When the reaction was completed as measured by TLC, extraction was carried out with dichloromethane and water. The organic layer was dried over anhydrous sodium sulfate, filtered, and concentrated. The concentrate was purified by column chromatography (Hexane:EtOAc=6:1→3:1→$CH_2Cl_2$) to afford the title compound (70.9 mg, 52%, yellow solid).

$^1$H NMR (400 MHz, $CDCl_3$) δ 7.86-7.83 (m, 3H), 7.76 (d, J=7.2 Hz, 1H), 7.54-7.39 (m, 6H), 7.38 (d, J=6.8 Hz, 2H), 6.16 (s, 1H), 4.97 (t, J=5.6 Hz, 1H), 4.46 (s, 2H), 4.26 (d, J=6.0 Hz, 2H), 2.51 (d, J=7.2 Hz, 2H), 1.87-1.77 (m, 1H), 0.88 (d, J=6.4 Hz, 6H)

$^{13}$C NMR (75 MHz, $CDCl_3$) δ 148.6, 144.6, 139.7, 133.1, 130.3, 129.2, 128.5, 128.2, 128.0, 127.7, 126.9, 126.6, 126.4, 125.8, 105.1, 59.2, 41.4, 35.2, 28.4, 22.4

Example 75

N-[{1-(4-Fluorophenyl)-5-isobutyl-1H-pyrazol-3-yl}methyl]-1-(naphthalen-2-yl) methanesulfonamide (Compound 25)

To a solution of naphthalen-2-ylmethanesulfonyl chloride (129 mg, 0.536 mmol) in dichloromethane (5 mL) were slowly added drops of {1-(4-fluorophenyl)-5-isobutyl-1H-pyrazol-3-yl}methaneamine (114 mg, 0.461 mmol) at 0° C. At the same temperature, triethylamine (0.07 mL, 0.507 mmol) was added before stirring for 2 hrs at room temperature. When the reaction was completed as measured by TLC, extraction was carried out with dichloromethane and water. The organic layer thus formed was dried over anhydrous sodium sulfate, filtered, and concentrated. The concentrate was purified by column chromatography (Hexane:EtOAc=4:1→$CH_2Cl_2$) to afford the title compound (27.0 mg, 13%, yellow solid).

$^1$H NMR (300 MHz, $CDCl_3$) δ 8.89 (brs, 1H), 7.83-7.66 (m, 4H), 7.54-7.49 (m, 2H), 7.45-7.36 (m, 3H), 7.21-7.14 (m, 2H), 6.07 (s, 1H), 4.50 (d, J=4.9 Hz, 2H), 4.17 (s, 2H), 2.49 (d, J=7.1 Hz, 2H), 1.87-1.78 (m, 1H), 0.90 (d, J=6.6 Hz, 6H)

$^{13}$C NMR (75 MHz, $CDCl_3$) δ 190.5, 163.7, 160.4, 146.9, 144.7, 135.9, 133.2, 133.1, 132.8, 128.8, 128.1, 127.9, 127.6, 127.5, 126.6, 126.5, 126.4, 116.3, 116.0, 116.3, 116.0, 104.9, 44.8, 44.0, 35.1, 28.4, 22.4

Example 76

1-(tert-Butyl)-5-{4-(piperidin-1-yl)phenyl}-1H-pyrazole-3-carboaldehyde

To a solution of ethyl-1-(tert-butyl)-5-{4-(piperidin-1-yl)phenyl}-1H-pyrazole-3-carboxylate (1.01 g, 3.46 mmol) in dichloromethane (10 mL) was added dropwise a diisobutylaluminum hydride solution (10.4 mL, 10.4 mmol, 1.0 M in toluene) at −78° C., followed by stirring for 1 hr. When the reaction was completed as measured by TLC, the reaction mixture was acidified to a pH of 2~3 with 3 M HCl. After extraction with dichloromethane, the extract was dried over anhydrous sodium sulfate, filtered, and concentrated. The concentrate was purified by column chromatography (Hexane:EtOAc=10:1) to afford the title compound (501 mg, 59%, yellow oil).

$^1$H NMR (300 MHz, $CDCl_3$) δ 9.76 (s, 1H), 7.61 (d, J=7.26 Hz, 2H), 6.82 (d, J=7.26 Hz, 2H), 6.78 (s, 1H), 3.46 (brs, 4H), 1.53 (brs, 4H), 1.35 (s, 9H)

Example 77

[1-(tert-Butyl)-5-{4-(piperidin-1-yl)phenyl}-1H-pyrazol-3-yl]methaneamine

To a solution of hydroxylamine hydrogen chloride (161 mg, 2.32 mmol) in dichloromethane (4 mL) was slowly added drops of triethylamine (0.33 mL, 2.32 mmol) at 0° C., followed by the slow addition of drops of a solution of 1-(tert-butyl)-5-{4-(piperidin-1-yl)phenyl}-1H-pyrazole-3-carboaldehyde (501 mg, 2.03 mmol) in dichloromethane (2 mL). The reaction mixture was stirred at room temperature for 1 hr. When the reaction was completed as measured by TLC, extraction was carried out with dichloromethane and water. The organic layer thus formed was dried over anhydrous sodium sulfate, filtered, and concentrated to afford 1-(tert-butyl)-5-{4-(piperidin-1-yl)phenyl}-1H-pyrazole-3-carboaldehyde oxime.

This oxime compound (487 mg, 1.86 mmol) was dissolved in a mixed solvent of diethyl ether (3 mL) and tetrahydrofuran (10 mL), and a lithium aluminum hydride solution (0.62 mL, 0.615 mmol, 1.0 M diethyl ether) was added dropwise at 0° C. The reaction mixture was stirred at room temperature for a day. When the reaction was completed as measured by TLC (Hexane:EtOAc=2:1), drops of $Na_2SO_4 \cdot 10H_2O$ were added at 0° C. After filtration through celite at a reduced pressure, the filtrate was concentrated to afford the title compound without further purification (422 mg, 92%, yellow oil).

$^1$H-NMR (300 MHz, $CDCl_3$) δ 8.68 (brs, 2H), 7.60 (d, J=7.26 Hz, 2H), 6.78 (d, J=7.26 Hz, 2H), 6.32 (s, 1H), 4.15 (s, 2H), 3.45 (brs, 4H), 1.50 (brs, 4H), 1.27 (s, 9H)

Example 78

N-{[1-(tert-Butyl)-5-{4-(piperidin-1-yl)phenyl-1H-pyrazol-3-yl]methyl}benzenesulfonamide (Compound 26)

To a solution of [1-(tert-butyl)-5-{4-(piperidin-1-yl)phenyl}-1H-pyrazol-3-yl]methaneamine in dichloromethane (6 mL) was added dropwise triethylamine (0.13 mL, 0.939 mmol) at 0° C., followed by the addition of drops of benzenesulfonyl chloride (213 mg, 0.896 mmol). The solution was stirred for 4 hrs at room temperature. When the reaction was completed as measured by TLC, extraction was carried out with dichloromethane and water. The organic layer thus formed was dried over anhydrous sodium sulfate, filtered, and concentrated. The concentrate was purified by column chromatography (Hexane:EtOAc=2:1→1:1) to afford the title compound (317 mg, 85%, white solid).

$^1$H NMR (300 MHz, $CDCl_3$) δ 7.86-7.71 (m, 3H), 7.62-7.59 (m, 4H), 6.82-6.80 (m, 2H), 6.31 (s, 1H), 5.38 (brs, 1H), 4.46 (s, 2H), 3.46 (brs, 4H), 1.53 (brs, 4H), 1.35 (s, 9H)

$^{13}$C NMR (75 MHz, $CDCl_3$) δ 147.9, 145.7, 144.6, 144.5, 131.8 130.3 130.1 129.0, 128.4, 105.2, 70.4, 54.8, 15.5, 40.2, 29.7

Example 79

1-(tert-Butyl)-5-[4-(cyclohexylphenyl)]-1H-pyrazole-3-carboaldehyde

To a solution of ethyl-1-(tert-butyl)-5-{4-(cyclohexylphenyl)-1H-pyrazole-3-carboxylate (1.01 g, 3.46 mmol) in dichloromethane (10 mL) was added a diisobutylaluminum hydride solution (10.4 mL, 10.4 mmol, 1.0 M in toluene) at −78° C., followed by stirring for 1 hr. When the reaction was completed as measured by TLC, the reaction mixture was acidified to a pH of 2~3 with 3 M HCl. After extraction with dichloromethane, the extract was dried over anhydrous sodium sulfate, filtered, and concentrated. The concentrate was purified by column chromatography (Hexane:EtOAc=10:1) to afford the title compound (501 mg, 59%, yellow oil).

$^1$H NMR (300 MHz, $CDCl_3$) δ 9.75 (s, 1H), 7.71 (d, J=7.26 Hz, 2H), 7.36 (d, J=7.26 Hz, 2H), 6.81 (s, 1H), 2.72 (brs, 3H), 1.86 (brs, 4H), 1.53 (m, 13H)

Example 80

[1-(tert-Butyl)-5-(4-cyclohexylphenyl)-1H-pyrazol-3-yl]methaneamine

To a solution of hydroxylamine hydrogen chloride (161 mg, 2.32 mmol) in dichloromethane (5 mL) were slowly added drops of triethylamine (0.33 mL, 2.32 mmol) at 0° C., followed by the slow addition of drops of a solution of 1-(tert-butyl)-5-[4-(cyclohexylphenyl)]-1H-pyrazole-3-carboaldehyde (501 mg, 2.03 mmol) in dichloromethane (2 mL). The resulting solution was stirred for 4 hrs at room temperature. When the reaction was completed as measured by TLC, extraction was carried out with dichloromethane and water. The organic layer thus formed was dried over anhydrous sodium sulfate, filtered, and concentrated to afford 1-(tert-butyl)-5-(4-cyclohexylphenyl)-1H-pyrazole-3-carboaldehyde oxime (487 mg, yellow liquid).

This oxime compound (487 mg, 1.86 mmol) was dissolved in a mixed solvent of diethyl ether (3 mL) and tetrahydrofuran (10 mL), and a lithium aluminum hydride solution (0.62 mL, 0.615 mmol, 1.0 M diethyl ether) was added dropwise at 0° C. The reaction mixture was stirred at room temperature for a day. When the reaction was completed as measured by TLC (Hexane:EtOAc=2:1), drops of $Na_2SO_4.10H_2O$ were added at 0° C. After filtration through celite at a reduced pressure, the filtrate was concentrated to afford the title compound without further purification (422 mg, 92%, yellow oil).

$^1$H NMR (300 MHz, $CDCl_3$) δ 8.60 (brs, 2H), 7.71 (d, J=7.26 Hz, 2H), 7.36 (d, J=7.26 Hz, 2H), 6.27 (s, 1H), 4.24 (s, 2H), 2.72 (brs, 1H), 1.86 (brs, 4H), 1.51 (brs, 4H), 1.35-1.27 (m, 15H)

Example 81

N-{[1-(tert-butyl)-5-(4-cyclohexylphenyl)-1H-pyrazol-3-yl]methyl}benzenesulfonamide (Compound 27)

To a solution of [1-(tert-butyl)-5-(4-cyclohexylphenyl)-1H-pyrazol-3-yl]methaneamine (211 mg, 0.853 mmol) in dichloromethane (6 mL) was added dropwise triethylamine (0.13 mL, 0.939 mmol) at 0° C., followed by the addition of drops of benzenesulfonyl chloride (213 mg, 0.896 mmol). The resulting solution was stirred at room temperature for 4. When the reaction was completed as measured by TLC, extraction was carried out with dichloromethane and water. The organic layer thus formed was dried over anhydrous sodium sulfate, filtered and concentrated. The concentrate was purified by column chromatography (Hexane:EtOAc=2:1→1:1) to afford the title compound (317 mg, 85%, white solid).

$^1$H NMR (300 MHz, $CDCl_3$) δ 7.86-7.62 (m, 4H), 7.71-7.68 (m, 3H), 7.36-7.31 (m, 2H), 6.27 (s, 1H), 2.72 (brs, 1H), 1.86 (brs, 4H), 1.32-1.24 (m, 15H)

$^{13}$C NMR (75 MHz, $CDCl_3$) δ 149.6, 147.9, 145.6, 144.6, 144.5, 131.9, 130.3 129.0, 128.4, 120.0, 112.7, 105.3, 70.4, 54.8, 40.8, 25.8, 24.5, 29.7

Example 82

1,2-Benzisothiazoline-1,1-dioxide

To a solution of 1,2-benzisothiazoline-3-one-1,1-dioxide (25, 554 mg, 3.02 mmol) in THF (8.0 mL) was slowly added lithium aluminum hydride (1M in ether, 4.09 mL, 4.09 mmol). The solution was stirred for 48 hrs, followed by the slow addition of drops of $Na_2SO_4$ $10H_2O$ at 0° C. The reaction mixture was filtered through celite, and the filtrate was concentrated to dryness to afford the title compound (182 mg, 35.6%).

$^1$H NMR (300 MHz, $CDCl_3$) δ 7.85 (d, J=7.65 Hz, 1H), 7.67 (d, J=7.49, 1.17 Hz, 1H), 7.58 (t, J=7.44 Hz, 1H), 7.44 (d, J=7.59 Hz, 1H), 4.74 (brs, 1H), 4.59 (s, 2H)

Example 83

2-((5-Isobutyl-1-phenyl-1H-pyrazol-3-yl)methyl)-2,3-dihydrobenzo[d]isothiazole-1,1-dioxide (Compound 28)

To a solution of 1,2-benzisothiazoline-1,1-dioxide (51.8 mg, 0.306 mmol) in N,N-dimethylformamide (1.0 mL) was added potassium carbonate (423 mg, 3.06 mmol), followed by stirring for 10 min. This solution was added with (5-isobutyl-1-phenyl-1H-pyrazol-3-yl)methyl bromide (108 mg, 0.367 mmol) in methylene chloride, and stirred for a day. Dilution was carried out in ethyl acetate before filtration. The filtrate was extracted with 1N HCl and an aqueous saturate sodium hydrogen carbonate solution. The organic layer was dried over magnesium sulfate, and concentrated in vacuo. The concentrate was purified by column chromatography (Hexane:EtOAc=3:1→2:1) to afford the title compound (99.8 mg, 85.5%).

$^1$H NMR (400 MHz, $CDCl_3$) δ 7.81-7.79 (m, 2H), 7.58-7.33 (m, 8H), 6.35 (s, 1H), 4.54 (s, 2H), 4.39 (s, 2H), 2.50 (d, J=7.06 Hz, 2H), 1.84-1.77 (m, 1H), 0.84 (d, J=6.56 Hz, 6H)

$^{13}$C NMR (100 MHz, $CDCl_3$) δ 147.2, 144.7, 139.7, 135.1, 134.0, 132.6, 129.2, 129.0, 128.1, 125.7, 124.6, 121.3, 106.0, 50.0, 41.3, 35.2, 28.3, 22.4

Example 84

2-[{1-(tert-Butyl)-5-isobutyl-1H-pyrazol-3-yl}methyl]-2,3-dihydro[d]isothiazole 1,1-dioxide (Compound 29)

To a solution of 1,2-benzisothiazoline-1,1-dioxide (70.4 mg, 0.416 mmol) in N,N-dimethylformamide (2 mL) was added potassium carbonate (578 mg, 4.16 mmol) at room temperature, followed by stirring for 10 min. This solution was slowly added with drops of {1-(tert-butyl)-5-isobutyl-1H-pyrazol-3-yl}methyl bromide (126 mg, 0.462 mmol) in methylene chloride (4 mL), and then stirred at room temperature for a day. When the reaction was completed as measured by TLC (Hexane:EtOAc=6:1), the reaction mixture was filtered through celite in vacuo. The filtrate was neutralized with 1M HCl and an aqueous saturate sodium hydrogen carbonate solution. After extraction with ethyl acetate and water, the organic layer thus formed was dried over anhydrous magnesium sulfate, filtered, and concentrated in vacuo. The concentrate was purified by column chromatography (Hexane:EtOAc=6:1) to afford the title compound (124 mg, 79%, white solid).

M.P. 102.5-105.4° C.;

$^1$H NMR (300 MHz, $CDCl_3$) δ 7.81 (d, J=6.6 Hz, 1H), 7.60-7.48 (m, 2H), 7.36 (d, J=7.4 Hz, 1H), 6.18 (s, 1H), 4.45 (s, 2H), 4.34 (s, 2H), 2.64 (d, J=7.1 Hz, 2H), 2.06-1.09 (m, 1H), 1.64 (s, 9H), 0.98 (d, J=6.6 Hz, 6H);

$^{13}$C NMR (75 MHz, $CDCl_3$) δ 143.62, 143.10, 135.4, 134.3, 132.5, 128.9, 124.5, 121.3, 106.7, 59.9, 49.9, 41.5, 37.3, 30.5, 28.4, 22.7

Example 85

2-[{1-(4-Fluorophenyl)-5-isobutyl-1H-pyrazol-3-yl}methyl]-2,3-dihydro[d]isothiazole 1,1-dioxide (Compound 30)

To a solution of 1,2-benzisothiazoline-1,1-dioxide (97.1 mg, 0.574 mmol) in N,N-dimethylformamide (3 mL) was added potassium carbonate (793 mg, 5.74 mmol) at room temperature, followed by stirring for 10 min. The solution was slowly added with drops of methylene chloride (5 mL) in {1-(4-fluorophenyl)-5-isobutyl-1H-pyrazol-3-yl}methyl bromide (199 mg, 0.638 mmol), and stirred for a day at room temperature. When the reaction was completed as measured by TLC (Hexane:EtOAc=3:1), the reaction mixture was filtered through celite. The filtrate was neutralized with 1M HCl and an aqueous saturate sodium hydrogen carbonate solution. After extraction with ethyl acetate and water, the organic layer was dried over magnesium sulfate, filtered, and concentrated in vacuo. The concentrate was purified by column chromatography (Hexane:EtOAc=6:1) to afford the title compound (124 mg, 79%, white solid).

M.P. 119.3-122.7° C.;

$^1$H NMR (300 MHz, CDCl$_3$) δ 7.83-7.49 (m, 3H), 7.41-7.34 (m, 3H), 7.20-7.14 (m, 2H), 6.35 (s, 1H), 4.52 (s, 2H), 4.39 (s, 2H), 2.46 (d, J=7.2 Hz, 2H), 1.87-1.73 (m, 1H), 0.84 (d, J=6.6 Hz, 6H);

$^{13}$C NMR (75 MHz, CDCl$_3$) δ 163.7, 160.4, 147.4, 144.8, 135.9, 135.1, 134.0, 132.7, 129.1, 127.7, 127.6, 124.6, 121.3, 116.2, 115.9, 106.1, 53.5, 50.0, 41.3, 35.1, 28.3, 22.4

Example 86

2-[{1-(2,6-Dichlorophenyl)-5-isobutyl-1H-pyrazol-3-yl}methyl]-2,3-dihydro[d]isothiazole 1,1-dioxide (Compound 31)

To a solution of N,N-dimethylformamide (1 mL) in 1,2-benzisothiazoline-1,1-dioxide (31.4 mg, 0.186 mmol) was added potassium carbonate (255 mg, 1.85 mmol) at room temperature, followed by stirring for 10 min. This solution was slowly added with drops of {1-(2,6-dichlorophenyl)-5-isobutyl-1H-pyrazol-3-yl}methyl bromide (73.3 mg, 0.202 mmol) in methylene chloride (2 mL), and stirred for a day at room temperature. When the reaction was completed as measured by TLC (Hexane:EtOAc=4:1), the reaction mixture was filtered through celite. The filtrate was neutralized with 1M HCl and an aqueous saturate sodium hydrogen carbonate solution. After extraction with ethyl acetate and water, the organic layer thus formed was dried over anhydrous magnesium sulfate, filtered, and concentrated in vacuo. The concentrate was purified by column chromatography (Hexane:EtOAc=2:1) to afford the title compound (61.9 mg, 74%, white solid).

M.P. 130.2-139.2° C.;

$^1$H NMR (300 MHz, CDCl$_3$) δ 7.84 (d, J=7.7 Hz, 1H), 7.62-7.30 (m, 6H), 6.40 (s, 2H), 4.57 (s, 2H), 4.38 (s, 2H), 2.24 (d, J=7.3 Hz, 2H), 1.92-1.79 (m, 1H), 0.89 (d, J=6.6 Hz, 6H);

$^{13}$C NMR (75 MHz, CDCl$_3$) δ 148.3, 146.4, 135.4, 135.2, 135.1, 134.2, 131.0, 129.0, 128.8, 124.6, 121.4, 105.4, 49.6, 41.3, 34.8, 27.5, 22.5

Example 87

2-[{1-(tert-butyl)-5-phenyl-1H-pyrazol-3-yl}methyl]-2,3-dihydro[d]isothiazole 1,1-dioxide (Compound 32)

To a solution of N,N-dimethylformamide (0.9 mL) in 1,2-benzisothiazoline-1,1-dioxide (10.6 mg, 0.063 mmol) was added potassium carbonate (83.9 mg, 0.607 mmol) at room temperature, followed by stirring for 10 min. This solution was slowly added with drops of {1-(tert-butyl)-5-phenyl-1H-pyrazol-3-yl}methyl bromide (18.7 mg, 0.064 mmol) in methylene chloride (3 mL), and stirred for a day at room temperature. When the reaction was completed as measured by TLC (Hexane:EtOAc=4:1), the reaction mixture was filtered through celite. The filtrate was neutralized with 1M HCl and an aqueous saturate sodium hydrogen carbonate solution. After extraction with ethyl acetate and water, the organic layer thus formed was dried over anhydrous magnesium sulfate, filtered, and concentrated in vacuo. The concentrate was purified by column chromatography (Hexane:EtOAc=6:1→2:1) to afford compound 23 (9.50 mg, 40%, white solid).

M.P 145.3-145.6° C.;

$^1$H NMR (300 MHz, CDCl$_3$) δ 7.86 (d, J=7.5 Hz, 1H), 7.65-7.52 (m, 2H), 7.43-7.35 (m, 2H), 6.27 (s, 1H), 4.54 (s, 2H), 4.47 (s, 2H), 1.49 (s, 9H);

$^{13}$C NMR (75 MHz, CDCl$_3$) δ 144.1, 143.5, 135.3, 134.3, 134.0, 132.5, 130.4, 129.0, 128.4, 127.8, 124.5, 121.5, 61.3, 50.0, 41.4, 31.2

Example 88

2-[{1-(tert-Butyl)-5-(4-fluorophenyl)-1H-pyrazol-3-yl}methyl]-2,3-dihydro[d]isothiazole 1,1-dioxide (Compound 33)

To a solution of 1,2-benzisothiazoline-1,1-dioxide (10.3 mg, 0.061 mmol) in N,N-dimethylformamide (0.9 mL) was added potassium carbonate (88.5 mg, 0.640 mmol) at room temperature, followed by stirring for 10 min. The solution was slowly added with drops of {1-(tert-butyl)-5-(4-fluorophenyl)-1H-pyrazol-3-yl}methyl bromide (20.9 mg, 0.067 mmol) in methylene chloride (3 mL), and stirred at room temperature for a day. When the reaction was completed as measured by TLC (Hexane:EtOAc=2:1), the reaction mixture was filtered through celite. The filtrate was neutralized with 1M HCl and an aqueous saturate sodium hydrogen carbonate solution. After extraction with ethyl acetate and water, the organic layer thus formed was dried over anhydrous magnesium sulfate, filtered, and concentrated in vacuo. The concentrate was purified by column chromatography (Hexane:EtOAc=6:1→1:1) to afford the title compound (10.2 mg, 42%, white solid).

M.P. 163.5-167.5° C.;

$^1$H NMR (300 MHz, CDCl$_3$) δ 7.86 (d, J=7.6 Hz, 1H), 7.65-7.53 (m, 2H), 7.41 (d, J=7.5 Hz, 1H), 7.35-7.29 (m, 2H), 7.13-7.06 (m, 2H), 6.27 (s, 1H), 4.53 (s, 2H), 4.46 (s, 2H), 1.48 (s, 9H);

$^{13}$C NMR (75 MHz, CDCl$_3$) δ 164.4, 162.3, 161.1, 143.6, 142.9, 135.3, 134.2, 132.6, 132.2, 132.1, 129.9, 129.0, 124.5, 121.5, 115.0, 114.7, 109.3, 61.3, 50.0, 41.3, 31.2

Example 89

2-[{1-(tert-Butyl)-5-(4-trifluoromethylphenyl)-1H-pyrazol-3-yl}methyl]-2,3-dihydro[d]isothiazole 1,1-dioxide (Compound 34)

To a solution of 1,2-benzisothiazoline-1,1-dioxide (24.3 mg, 0.144 mmol) in N,N-dimethylformamide (1 mL) was added dropwise potassium carbonate (180 mg, 1.30 mmol) at room temperature, followed by stirring for 15 min. This solution was slowly added with drops of {1-(tert-butyl)-5-(4-trifluoromethylphenyl)-1H-pyrazol-3-yl}methyl bromide (51.6 mg, 0.143 mmol) in methylene chloride (4.5 mL), and stirred for a day at room temperature. When the reaction was completed as measured by TLC (Hexane:EtOAc=4:1), the reaction mixture was filtered through celite. The filtrate was neutralized with 1M HCl and an aqueous saturate sodium hydrogen carbonate solution. After extraction with ethyl acetate and water, the organic layer thus formed was dried over anhydrous magnesium sulfate, filtered, and concentrated in vacuo. The concentrate was purified by column chromatography (Hexane:EtOAc=4:1→2:1) to afford the title compound (25.4 mg, 39%, white solid).

M.P. 144.6-148.2° C.;

$^1$H NMR (300 MHz, CDCl$_3$) δ 7.85 (d, J=7.7 Hz, 1H), 7.68-7.48 (m, 6H), 7.41 (d, J=7.4 Hz, 1H), 6.29 (s, 1H), 4.54 (s, 2H), 4.47 (s, 2H), 1.49 (s, 9H);

$^{13}$C NMR (75 MHz, CDCl$_3$) δ 143.9, 142.4, 137.9, 135.3, 134.2, 132.6, 130.9, 130.8, 130.5, 129.0, 125.7, 124.8, 124.7, 124.5, 122.1, 121.5, 109.4, 61.5, 50.1, 41.3, 31.3

Example 90

2-[{1-(tert-Butyl)-5-(4-piperidin-1-yl-phenyl)-1H-pyrazol-3-yl}methyl]-2,3-dihydro[d]isothiazole 1,1-dioxide (Compound 35)

To a solution of {1-(tert-butyl)-5-(4-piperidin-1-yl-phenyl)-1H-pyrazol-3-yl}methanol (54.9 mg, 0.175 mmol) in methylene chloride (1.5 mL) were added PPh$_3$ (93.1 mg, 0.355 mmol) and CBr$_4$ (121 mg, 0.365 mmol) at 0° C., followed by stirring at the same temperature for one hour to give {1-(tert-butyl)-5-(4-piperidin-1-yl-phenyl)-1H-pyrazol-3-yl}methyl bromide. When the reaction was completed as measured by TLC(Hexane:EtOAc=2:1), 1,2-benzisothiazoline-1,1-dioxide (27.3 mg, 0.161 mmol) in N,N-dimethylformamide (1.5 mL) was added dropwise. At the same temperature, potassium carbonate (228 mg, 1.65 mmol) was added, and the resulting solution was stirred for a day. When the reaction was completed as measured by TLC (Hexane:EtOAc=2:1), water was added, after which extraction was carried out with ethyl acetate and brine. The organic layer thus formed was dried over anhydrous magnesium sulfate, and concentrated in vacuo. The concentrate was purified by column chromatography (Hexane:EtOAc=4:1→1:1) to afford the title compound (15.2 mg, 20%, white solid).

M.P. 150.4-165.2° C.;

$^1$H NMR (300 MHz, CDCl$_3$) δ 7.89 (d, J=7.9 Hz, 1H), 7.64-7.52 (m, 2H), 7.40 (d, J=7.1 Hz, 1H), 7.30-7.17 (m, 2H), 6.29 (d, J=8.7 Hz, 2H), 6.22 (s, 1H), 4.52 (s, 2H), 4.46 (s, 2H), 3.26-3.23 (brs, 4H), 1.79-1.74 (brs, 4H), 1.67-1.63 (brs, 2H), 1.49 (s, 9H);

$^{13}$C NMR (75 MHz, CDCl$_3$) δ 151.9, 144.4, 143.3, 135.4, 134.3, 132.5, 131.1, 128.9, 124.5, 123.7, 121.4, 114.9, 109.0, 61.0, 50.0, 41.4, 31.2, 25.7, 24.3

Example 91

2-[{1-(tert-Butyl)-5-(4-cyclohexylphenyl)-1H-pyrazol-3-yl}methyl]-2,3-dihydro[d]isothiazole 1,1-dioxide (Compound 36)

To a solution of {1-(tert-butyl)-5-(4-cyclohexylphenyl)-1H-pyrazol-3-yl}methanol (101 mg, 0.323 mmol) in were added PPh$_3$ (71.8 mg, 0.655 mmol), and CBr$_4$ (217 mg, 0.655 mmol) at 0° C., followed by stirring at the same temperature for one hour to give {1-(tert-butyl)-5-(4-cyclohexylphenyl)-1H-pyrazol-3-yl}methyl bromide. When the reaction was completed as measured by TLC (Hexane:EtOAc=2:1), drops of N,N-dimethylformamide (1.5 mL) in 1,2-benzisothiazoline-1,1-dioxide (57.1 mg, 0.388 mmol) were slowly added.

At the same temperature, potassium carbonate (447 mg, 3.23 mmol) was added, and the resulting solution was stirred for a day. When the reaction was completed as measured by TLC (Hexane:EtOAc=2:1), water was added dropwise, after which extraction was carried out with ethyl acetate and brine. The organic layer was dried over anhydrous magnesium sulfate, filtered, and concentrated in vacuo. The concentrate was purified by column chromatography (Hexane:EtOAc=4:1) to afford the title compound (55.4 mg, 31%, white solid).

M.P. 135.7-141.5° C.;

$^1$H NMR (300 MHz, CDCl$_3$) δ 7.83 (d, J=7.5 Hz, 1H), 7.63-7.50 (m, 2H), 7.40 (d, J=7.5 Hz, 1H), 7.30-7.20 (m, 4H), 6.24 (s, 1H), 4.53 (s, 2H), 4.45 (s, 2H), 2.56 (brs, 1H), 1.92-1.77 (m, 5H), 1.48-1.27 (m, 14H);

$^{13}$C NMR (75 MHz, CDCl$_3$) δ 148.5, 144.3, 143.4, 135.4, 134.3, 132.5, 131.3, 130.3, 128.9, 126.2, 124.5, 121.4, 109.0, 61.1, 50.0, 44.3, 41.4, 34.4, 31.2, 26.9, 26.1

Example 92

2-{(1-Isobutyl-5-phenyl-1H-pyrazol-3-yl)methyl}-2,3-dihydro[d]isothiazole 1,1-dioxide (Compound 37)

To a solution of (1-isobutyl-5-phenyl-1H-pyrazol-3-yl)methanol (52.1 mg, 0.226 mmol) in methylene chloride (1 mL) were added PPh$_3$ (146 mg, 0.557 mmol), CBr$_4$ (185 mg, 0.557 mmol) at 0° C., followed by stirring at the same temperature for 30 min to give (1-isobutyl-5-phenyl-1H-pyrazol-3-yl)methyl bromide. When the reaction was completed as measured by TLC (Hexane:EtOAc=4:1), a solution of 1,2-benzisothiazoline-1,1-dioxide (57.1 mg, 0.388 mmol) in N,N-dimethylformamide (1.5 mL) was added dropwise.

Then, drops of potassium carbonate (313 mg, 2.26 mmol) were added at the same temperature to the solution that was then stirred for 3 days. When the reaction was completed as measured by TLC (Hexane:EtOAc=2:1), water was dropped to the reaction mixture. After extraction with ethyl acetate and brine, the organic layer was dried over anhydrous magnesium sulfate, filtered, and concentrated in vacuo. The concentrate was purified by column chromatography (Hexane:EtOAc=2:1) to afford the title compound (37.8 mg, 44% %, white solid).

M.P 129.7-137.3° C.;

$^1$H NMR (300 MHz, CDCl$_3$) δ 7.86-7.63 (m, 1H), 7.63-7.51 (m, 2H), 7.49-7.37 (m, 6H), 6.42 (s, 1H), 4.56 (s, 2H), 4.41 (s, 2H), 3.96 (d, J=7.5 Hz, 2H), 2.24-2.15 (m, 1H), 0.79 (d, J=6.7 Hz, 6H);

$^{13}$C NMR (75 MHz, CDCl$_3$) δ 145.9, 145.6, 136.8, 135.2, 134.0, 133.0, 132.6, 130.8, 129.0, 128.7, 124.6, 121.4, 106.1, 56.8, 49.9, 41.3, 29.6, 19.8

Example 93

2-[{5-(4-Fluorophenyl)-1-isobutyl-1H-pyrazol-3-yl}methyl]-2,3-dihydro[d]isothiazole 1,1-dioxide (Compound 38)

To a solution of {5-(4-fluorophenyl)-1-isobutyl-1H-pyrazol-3-yl}methanol (19.4 mg, 0.078 mmol) in methylene chloride (1 mL) were added PPh$_3$ (42.8 mg, 0.163 mmol) and CBr$_4$ (66.3 mg, 0.200 mmol) at 0° C., followed by stirring at the same temperature for 30 minute to give {5-(4-fluorophenyl)-1-isobutyl-1H-pyrazol-3-yl}methyl bromide. When the reaction was completed as measured by TLC (Hexane:EtOAc=2:1), drops of 1,2-benzisothiazoline-1,1-dioxide (24.3 mg, 0.078 mmol) N,N-dimethylformamide (1.5 mL) were slowly added to the solution.

Then, potassium carbonate (113 mg, 0.816 mmol) were added at the same temperature, and the resulting solution was stirred for a day. When the reaction was completed as measured by TLC (Hexane:EtOAc=2:1), water was added, after which extraction was carried out with ethyl acetate and brine. The organic layer thus formed was dried over anhydrous magnesium sulfate, filtered, and concentrated in vacuo. The concentrate was purified by column chromatography (Hexane:EtOAc=2:1) to afford the title compound (19.2 mg, 62% %, white solid).

M.P. 110.8-118.2° C.;

$^1$H NMR (300 MHz, CDCl$_3$) δ 7.61-7.52 (m, 2H), 7.46-7.33 (m, 4H), 7.18-7.12 (m, 2H), 6.41 (s, 1H), 4.56 (s, 2H), 4.41 (s, 2H), 3.91 (d, J=7.5 Hz, 2H), 2.26-2.08 (m, 1H), 0.80 (d, J=6.7 Hz, 6H);

$^{13}$C NMR (75 MHz, CDCl$_3$) δ 146.0, 144.5, 136.8, 135.2, 134.0, 133.0, 132.6, 131.0, 130.8, 129.2, 129.1, 124.8, 124.5, 121.4, 115.9, 115.6, 106.3, 56.7, 49.9, 45.7, 41.2, 29.6, 19.8

Formulation Examples

The novel compound, represented by Chemical Formula 1, of the present invention can be formulated into various forms according to purpose. Non-limiting, several formulations containing the compound of Chemical formula 1 as active ingredient are illustrated in the following Examples.

Formulation 1: Tablet (Direct Compression)

After being sieved, 5.0 mg of an active ingredient was mixed with 14.1 mg of lactose, 0.8 mg of CrossPovidone USNF, and 0.1 mg of magnesium stearate, and compressed into a tablet.

Formulation 2: Tablet (Wet Granulation)

After being sieved, 5.0 mg of an active ingredient was mixed with 16.0 mg of lactose and 4.0 mg of starch. A solution of 0.3 mg of Polysolvate 80 in pure water was added in a suitable amount to the mixture, followed by microgranulation. The microgranules were dried, sieved, and mixed with 2.7 mg of colloidal silicon dioxide and 2.0 mg of magnesium stearate. Compression of the mixture afforded a tablet.

Formulation 3: Powder and Capsule

After being sieved, 5.0 mg of an active ingredient was mixed with 14.8 mg of lactose, 10.0 mg of polyvinyl pyrrolidone, and 0.2 mg of magnesium stearate. The compound was loaded into a hard No. 5 gelatin capsule using an appropriate device.

Formulation 4: Injection

Injection was prepared by dissolving 100 mg of an active ingredient, together with 180 mg of mannitol and 26 mg of Na$_2$HPO$_4$.12H$_2$O, in 2947 mg of distilled water.

Test Examples

Assay for Antagonistic Activity Against T-Type Calcium Ion Channel

The novel compounds, represented by Chemical Formula 1, of the present invention were assayed for antagonistic activity against T-type calcium ion channels as follows.

After being synthesized, the compounds were primarily screened for inhibitory activity against T-type channels using a high-throughput screening device FDSS6000, and selection was made of the synthetic compounds that blocked T-type channels at an inhibitory rate of 40% or higher. In a secondary screening process, the selected compounds were examined for the effective inhibitory concentration IC$_{50}$ by measuring Ca$^{2+}$ potentials in human HEK293 cells.

1) Screening for Inhibitory Activity Against T-Type Calcium Ion Channels Using FDSS6000

Using Titertek Multidrop Plate Dispenser, HEK293 cell line cells that stably expressed alG T-type calcium ion channel and Kir2.1 ($\alpha_{1G}$ cell line: KCTC 10519BP, Korean Human Gene Bank of the Korea Research Institute of Bioscience and Biotechnology) were seeded at a density of 4×10$^4$ cells/well into 96-well plates that were treated with poly-L-lysine (0.05 mg/ml) 12~24 hrs before activity screening. On the day of test, the cells adherent to the 96-well plates were washed three times with a HEPES buffer (150 mM NaCl, 5 mM KCl, 1 mM MgCl$_2$, 2 mM CaCl$_2$, 10 mM HEPES, 10 mM glucose, pH 7.4) using a 96-well plate washer (Bio Tek), and then stained with a fluorescent dye by treatment with a HEPES containing 5 µM fluo-3/AM and 0.001% Pluronic F-127 for 1 hr at room temperature. Again, the cells were washed twice with a HEPES buffer. Ten minutes before reading on FDSS6000, the cells were washed once with a HEPES buffer containing 10 mM CaCl$_2$, and the final volume per well was adjusted to 81 µL. Separately from the 96-well plates in which cells were contained, two 96-well plates were prepared so as to contain KCl (final concentration 75 mM), which activates T-type calcium ion channels, and blocker drugs therein. Since most cell-based HTS devices, although provided with a liquid application system necessary for drug infusion, have no liquid absorption systems, blocker drugs to be searched for and KCl were individually prepared into a 5-fold higher concentration in 27 µL of 10 mM CaCl$_2$ HEPES. The concentration was 1/5 diluted into a final volume of 135 µL in each well before measurement. For the FDSS6000 measurements, cells were pre-incubated with drugs for 75 seconds after the 20-sec baseline recordings, and a change in intracellular calcium concentration induced by KCl was measured. The percent inhibition by a test compound was calculated as integrated values of 340/380 fluorescent ratio of untreated and drug-treated cells.

For accurate calcium-imaging, the light source of 4 xenon lamps in FDSS6000 were irradiated to make the cells exposed selectively to the excitation wavelength (340 nm and 380 nm) by computer-controlled filter wheel. Data was obtained at regular intervals of each 1.23 second. The emitter fluorescence light flew in through a long-pass filter was obtained as an average 340/380 ratio value for each well in the 96-wells by using CCD camera and digital fluorescence analyzer in FDSS6000. All image data and analyses were obtained by using FDSS6000-exclusive program provide from Hamamatsu Photonics.

2) Measurement of T-Type Calcium Ion Channel Activity in HEK293 Cells Using Electrophysiological Whole Cell Patch Clamp Method Dulbecco's modified Eagle's medium (DMEM) supplemented with 10% fetal bovine serum (FBS) and 1% penicillin/streptomycin (v/v) was employed. The cells were cultured at 36.5° C. in a humidified condition of 95% air/5% CO$_2$ in an incubator. The medium was refreshed every 3 or 4 days while the cells were sub-cultured every week, with the growth of only $\alpha_{1G}$ T-type calcium ion channel-expressing cells in the presence of G-418 (0.5 mg/mL). The recording to the cells used in the T-type calcium channel activity analysis was conducted 2-7 days after the cells were culturing on a cover slip coated with poly-L-lysine (0.5 mg/mL) when conducting every sub-culture. For analysis at a single cell level, the T-type calcium channel current was measured by an electrophysiological whole cell patch clamp method using EPC-9 amplifier (HEKA, German). For use in analyzing T-type calcium channel activity, an extracellular contained 140 mM NaCl, 2 mM CaCl$_2$, and 10 mM HEPES (pH 7.4) and an intracellular solution contained 130 mM KCl, 10 mM HEPES, 11 mM EDTA, and 5 mM MgATP (pH 7.4). The activation protocol for T-type calcium channels that are activated at low voltage is as follows: A micro glass electrode with a resistance of 3-4 M MΩ that was filled with the above prepared intracellular solution was pricked into a single cell to make a whole-cell recording mode. Thereafter, the cell membrane potential was fixed to −100 mV, and then the inward currents of T-type calcium channels were evoked by the test pulses of −30 mV for 50 ms at a holding potential of −100 mV every 10 seconds. Each compound was dissolved in 100% dimethyl sulfoxide (DMSO) to make a 10 mM stock solution. The effect of the compound on T-type calcium channel current was initially examined in a 10 μM (containing 0.1% DMSO) solution, which was 1000-fold diluted from the stock solution, and then in solutions that were likely to exhibit the inhibition effects for $IC_{50}$ (mostly in the range of 0.1 to 100 μM). More specifically, the cells were treated each compound, together with the extracellular solution, for 30 to 60 seconds, and the inhibition level of the inward peak currents by a test compound was calculated as a percentage from which the $IC_{50}$ values were determined. The results are summarized in the Table 1.

TABLE 1

| Test Compound | Inhibition % $\alpha_{1G}$ (10 μM) | Inhibition % $\alpha_{1H}$ (10 μM) |
|---|---|---|
| Compound 1 | 61.42 | 63.86 |
| Compound 2 | 64.10 | 62.72 |
| Compound 3 | 57.57 | 55.74 |
| Compound 4 | 57.26 | 62.21 |
| Compound 7 | 65.69 | 70.73 |
| Compound 10 | 29.78 | 61.36 |
| Compound 11 | 54.86 | 70.04 |
| Compound 13 | 45.09 | 69.31 |
| Compound 15 | 70.53 | 68.61 |
| Compound 16 | 74.24 | 72.00 |
| Compound 20 | 45.62 | 54.62 |
| Compound 28 | 67.87 | 75.51 |
| Compound 29 | 60.62 | 68.04 |
| Compound 30 | 70.81 | 71.57 |
| Compound 36 | 45.62 | 54.62 |
| Comparative Cpd. | — | 23.03 |

[Comparative Compound]

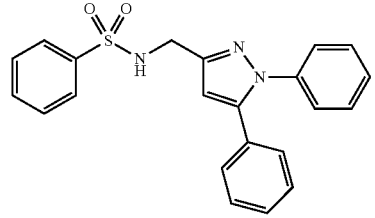 [SMILES: O=S(=O)(NCc1cc(-c2ccccc2)n(-c2ccccc2)n1)c1ccccc1]

The comparative compound, disclosed in WO2005/073197, is structurally different from the compound of the present invention in that it has two phenyl groups at both N1 and C5 positions of its pyrazole moiety. Due to this chemical structural difference, the comparative compound was found to have no activity as a T-type calcium ion channel antagonist.

3) In Vivo Assay for Suppressive Activity of Neuropathic Pain in Animal Model

Of 30 rats, 19 were selected by behavioral test, and neuropathic pain was induced in them by surgery. Two weeks later, a behavioral test was performed to confirm the perfect induction of neuropathic pain in 13 rats. They were randomly grouped, together with the other rats that were not in this behavioral test because of insufficient or no introduction of neuropathic pain. Gabapentin was orally administered at a dose of 100 mg/kg to 4 rats while the compound of the present invention was orally administered at a dose of 100 mg/kg to the other 6 rats in the same group.

Figure 2:
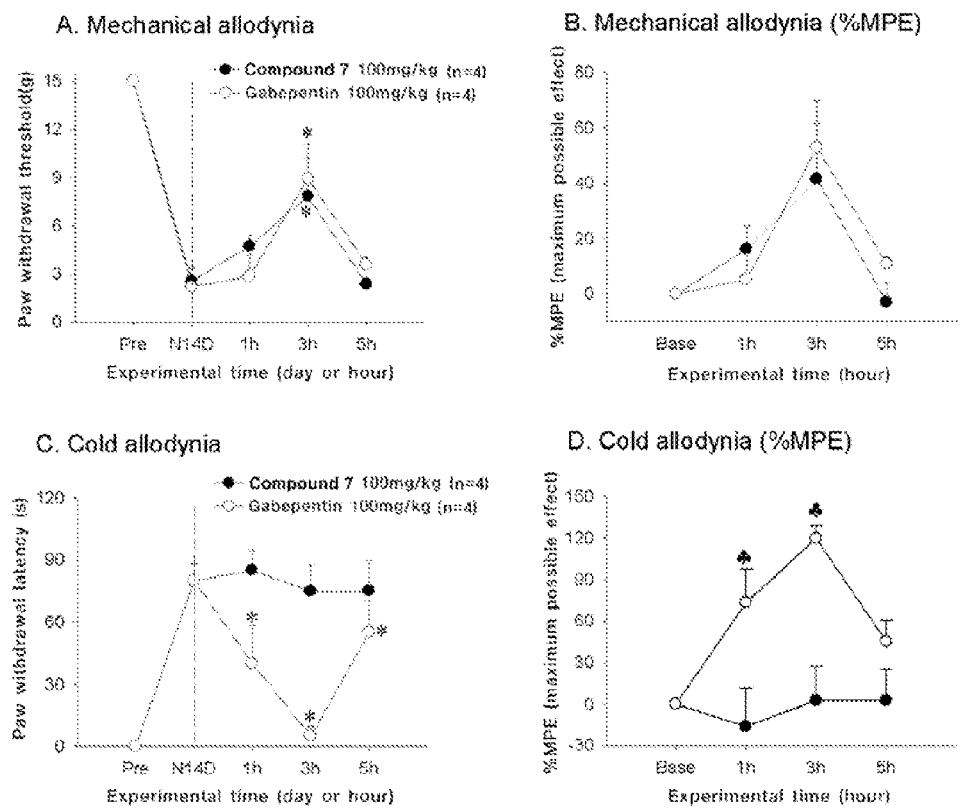
FIG. 2 shows therapeutic effect of the compound 7 according to the present invention on mechanical allodynia and cold allodynia, in comparison with gabapentin.

Therapeutic effects of Compound 1 and 7 of the present invention are depicted in FIGS. 1 and 2, respectively.

Anticancer Effect Screening Test

1) Culture of Cancer Cells

The cancer cell lines HT-1080 (Human Fibroblastoma) U87-MG (Human Glioma), LNCap (Human Prostate Carcinoma), and KYSE410 (Human Esophageal Carcinoma) were employed for assaying test compounds for anticancer activity. These cancer cells, all derived from humans, were purchased from the Korean Cell Line Bank, and maintained in RPMI 1640 supplemented with 10% fetal bovine serum in an incubator (37° C., 5% $CO_2$), with a cell passage with 0.25% trypsin-1 mM EDTA every three days.

2) Measurement of Anticancer Activity

The SRB (sulforhodamine B) assay method, which was developed in 1989 by the National Cancer Institute to evaluate drugs for in vitro anticancer activity, was used to measure the growth of cancer cells.

For this assay, the cells at passages were separated from the surfaces of well plates using a trypsin-EDTA solution, and seeded at a density of 5×10³ cells/well into 96-well plates. After 24 hrs of incubation in a $CO_2$ incubator, the medium was removed. A 4-fold dilution of each of the compounds was added in an amount of 100 μL to each well, and the cells were incubated for 48 hrs. The cells were fixed by adding 100 μL of formalin to each well, washed five times with distilled water, dried at room temperature. The cells in each well were stained with 100 μL of 0.4% SRB for 30 min. at room temperature, washed five times with 1% acetic acid, and dried at room temperature. The bound protein stain was solubilized with 200 μL of 10 mM Trizma base (pH 10.5) in each well. The optical density was read at 540 nm.

To calculate pharmaceutical efficacy of test compounds in cancer cells, $GI_{50}$ was calculated according to the following Equation 1 or 2:

$$\text{Anticancer Activity (\%)} = \frac{T_2 - T_0}{T_0} \times 100 \ (\text{if } T_2 > T_0) \quad \text{(Equation 1)}$$

(wherein $T_0$ is the number of cells before the addition of a test compound, and $T_2$ is the number of cells after 48 hrs of incubation in the presence of a test compound)

$$\text{Anticancer Activity (\%)} = \frac{T_2 - T_0}{C - T_0} \times 100 \ (\text{if } T_2 = T_0 \text{ or } T_2 < T_0) \quad \text{(Equation 2)}$$

(wherein $T_0$ is the number of cells before the addition of a test compound, $T_2$ is the number of cells after 48 hrs of incubation in the presence of a test compound, and C is the number of cells after 48 hrs of incubation in the absence of test compounds).

The inhibition of cancer cell growth by the test compound (% inhibition) was determined by data regression using the Lotus program from the values calculated according to Equation 1, and the $IC_{50}$ value was calculated from the % inhibition. The result is summarized in Table 2.

TABLE 2

| Test Compound | Inhibition % for Cancer Cell (100 mM) | | | |
|---|---|---|---|---|
| | HT1080 | U87-MG | LNCap | KYSE410 |
| Compound 3 | 91.49 | 93.73 | 93.38 | 94.35 |
| Compound 6 | 90.42 | 92.08 | 93.04 | 88.69 |
| Compound 8 | 86.81 | 64.42 | 85.42 | 61.36 |
| Compound 11 | 57.56 | 34.40 | 71.41 | 47.30 |
| Compound 14 | 39.49 | 39.80 | 72.45 | 43.53 |
| Compound 16 | 76.37 | 52.42 | 85.00 | 61.64 |
| Compound 18 | 89.03 | 92.15 | 91.38 | 87.28 |
| Compound 19 | 56.90 | 39.10 | 76.64 | 35.52 |
| Compound 20 | 61.73 | 32.34 | 81.28 | 39.07 |
| Gleevec | 92.04 | 86.51 | 82.56 | 75.92 |
| Tarceva | 83.07 | 55.96 | 47.12 | 36.30 |
| Iressa | 94.41 | 88.88 | 91.30 | 18.69 |

INDUSTRIAL APPLICABILITY

Exhibiting excellent activity as a T-type calcium channel antagonist, as described above, the N-(pyrazolylmethyl)arylsulfonamide derivatives represented by Chemical Formula 1 or a pharmaceutically acceptable salts thereof in accordance with the present invention can be useful for treating and preventing cerebral diseases, cardiac diseases, cancers and pain-related diseases.

Accordingly, the compound of the present invention can effectively block T-type calcium ion channels, finding useful applications in the treatment or prevention of various diseases including cerebral diseases such as epilepsy, depression, dementia, sleep disorder, diabetes, obesity, etc.; cardiac diseases such as hypertension, cardiac arrhythmia, angina pectoris, myocardial infarction, congestive heart failure, etc.; cancers such as liver cancer, lung cancer, colon cancer, prostate cancer, breast cancer, uterine cancer, esophageal cancer, brain cancer, etc.; and pain-related diseases such as chronic and acute pain, neuropathic pain, etc.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A compound selected from the group consisting of a N-(pyrazolylmethyl)arylsulfonamide derivative represented by the following Chemical Formula 1, and a pharmaceutically acceptable salt thereof:

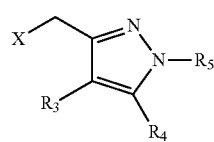

(1)

wherein,
X is

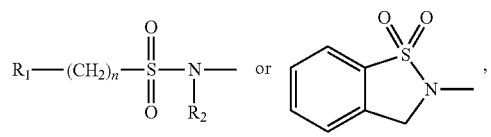

wherein $R_1$ represents $C_6$~$C_{12}$ aryl, substituted with one to three substituents selected from the group consisting of halo, $C_1$~$C_6$ alkyl and piperidin-1-yl, or unsubstituted; or 5- to 12-membered heteroaryl with 1 to 3 nitrogen atoms, $R_2$ represents a hydrogen atom; or $C_1$~$C_6$ alkyl, $R_3$ represents a hydrogen atom; or $C_1$~$C_6$ alkyl, $R_4$ and $R_5$ independently represent $C_1$~$C_6$ alkyl; or phenyl, substituted with a substituent selected from the group consisting of halo, $C_1$~$C_6$ alkyl, $C_1$~$C_6$ haloalkyl, and piperidin-1-yl, or unsubstituted, with the proviso that any one of $R_4$ and $R_5$ is substituted or unsubstituted phenyl while the other represents $C_1$~$C_6$ alkyl, and n is an integer of 0 to 6.

2. The compound of claim 1, wherein the compound is selected from the group consisting of an N-(pyrazolylmethyl)arylsulfonamide derivative represented by the following Chemical Formula 1a, and a pharmaceutically acceptable salt thereof:

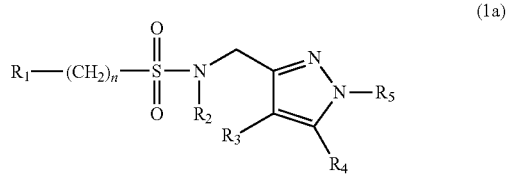

(1a)

wherein, $R_1$ represents phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-methylphenyl, 4-tert-butylphenyl, 2-fluoro-5-methylphenyl, 2-methyl-3-chlorophenyl, 4-cyclohexylphenyl, 4-(piperidin-1-yl)phenyl, naphthalen-1-yl, naphthalen-2-yl, or quinolin-8-yl;

$R_2$ and $R_3$, which may be the same or different, represent a hydrogen atom, methyl, or ethyl;

when $R_4$ is methyl, ethyl, propyl, isopropyl, butyl, isobutyl, or tert-butyl, $R_5$ represents phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl;

When $R_5$ is phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl, $R_5$ represents methyl, ethyl, propyl, isopropyl, butyl, isobutyl, or tert-butyl; and n represents 0, 1, or 2.

3. The compound of claim 1, wherein the compound is selected from the group consisting of an N-(pyrazolylmethyl)arylsulfonamide derivative represented by the following Chemical Formula 1b, and a pharmaceutically acceptable salt thereof:

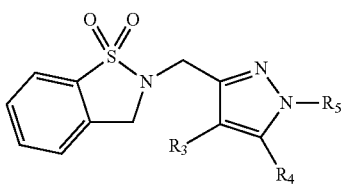

(Ib)

wherein

R₃ represents a hydrogen atom, methyl, or ethy;

when R₄ is methyl, ethyl, propyl, isopropyl, butyl, isobutyl, or tert-butyl, R₅ represents phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl; and when R₄ is phenyl, 3-fluorophenyl, 3-chlorophenyl, 3-iodophenyl, 4-fluorophenyl, 4-chlorophenyl, 4-iodophenyl, 2,6-difluorophenyl, 2,6-dichlorophenyl, 4-trifluoromethylphenyl, 4-cyclohexylphenyl, or 4-(piperidin-1-yl)phenyl, R₅ represents methyl, ethyl, propyl, isopropyl, butyl, isobutyl, or tert-butyl.

4. The compound of claim 1, being selected from the group consisting of:

N-[(5-isobutyl-1-phenyl-1H-pyrazol-3-yl)methyl]benzenesulfonamide (Compound 1),

N-[(5-isobutyl-1-phenyl-1H-pyrazol-3-yl)methyl]-3-fluorobenzenesulfonamide (Compound 2), N-[(5-isobutyl-1-phenyl-1H-pyrazol-3-yl)methyl]-3-chlorobenzenesulfonamide (Compound 3), N-[(5-isobutyl-1-phenyl-1H-pyrazol-3-yl)methyl]-4-methylbenzenesulfonamide (Compound 4);

N-[(5-isobutyl-1-phenyl-1H-pyrazol-3-yl)methyl]-4-iodobenzenesulfonamide (Compound 5);

N-[(5-isobutyl-1-phenyl-1H-pyrazol-3-yl)methyl]-4-tert-butylbenzenesulfonamide (Compound 6);

N-[(5-isobutyl-1-phenyl-1H-pyrazol-3-yl)methyl]benzylsulfonamide (Compound 7);

N-[(5-isobutyl-1-phenyl-1H-pyrazol-3-yl)methyl]naphthalene-1-sulfonamide (Compound 8);

N-[(5-isobutyl-1-phenyl-1H-pyrazol-3-yl)methyl]naphthalene-2-sulfonamide (Compound 9);

N-[(5-isobutyl-1-phenyl-1H-pyrazol-3-yl)methyl]quinoline-8-sulfonamide (Compound 10);

N-[(5-isobutyl-1-phenyl-1H-pyrazol-3-yl)methyl]-(2-fluoro-5-methyl)benzenesulfonamide (Compound 11);

N-[(5-isobutyl-1-phenyl-1H-pyrazol-3-yl)methyl]-(2-methyl-3-chloro)benzenesulfonamide ((Compound 12);

N-[(5-isobutyl-1-phenyl-1H-pyrazol-3-yl)methyl]-2,6-difluorobenzenesulfonamide ((Compound 13);

N-[(5-isobutyl-1-phenyl-1H-pyrazol-3-yl)methyl]-2,6-dichlorobenzenesulfonamide (Compound 14);

N-[(5-isobutyl-4-methyl-1-phenyl-1H-pyrazol-3-yl)methyl]benzenesulfonamide (Compound 15);

N-[(5-isobutyl-4-methyl-1-phenyl-1H-pyrazol-3-yl)methyl]naphthalene-2-sulfonamide (Compound 16);

N-[(5-isobutyl-4-ethyl-1-phenyl-1H-pyrazol-3-yl)methyl]benzenesulfonamide (Compound 17);

N-methyl-N-[(5-isobutyl-1-phenyl-1H-pyrazol-3-yl)methyl]benzenesulfonamide (Compound 18);

N-[(5-isobutyl-1-phenyl-1H-pyrazol-3-yl)methyl]-2-phenylethanesulfonamide (Compound 19);

N-[(5-isobutyl-1-(4-fluorophenyl)-1H-pyrazol-3-yl)methyl]benzenesulfonamide (Compound 20);

N-[{1-(4-fluorophenyl)-5-isobutyl-1H-pyrazol-3-yl}methyl]quinoline-8-sulfonamide (Compound 21);

N-[{1-(tert-butyl)-5-(4-fluorophenyl)-1H-pyrazol-3-yl}methyl]benzenesulfonamide (Compound 22);

N-[{1-(tert-butyl)-5-phenyl-1H-pyrazol-3-yl}methyl]benzenesulfonamide (Compound 23);

N-(5-isobutyl-1-phenyl-1H-pyrazol-3-yl)-1-(naphthalen-2-yl)methanesulfonamide (Compound 24);

N-{1-(4-fluorophenyl)-5-isobutyl-1H-pyrazol-3-yl}-1-(naphthalen-2-yl)methanesulfonamide (Compound 25);

N-{[1-(tert-butyl)-5-{4-(piperidin-1-yl)phenyl-1H-pyrazol-3-yl]methyl}benzenesulfonamide (Compound 26);

N-{[1-(tert-butyl)-5-(4-cyclohexylphenyl)-1H-pyrazol-3-yl]methyl}benzenesulfonamide (Compound 27);

2-((5-isobutyl-1-phenyl-1H-pyrazol-3-yl)methyl)-2,3-dihydrobenzo[d]isothiazole-1,1-dioxide (Compound 28);

2-[{1-(tert-butyl)-5-isobutyl-1H-pyrazol-3-yl}methyl]-2,3-dihydro[d]isothiazole 1,1-dioxide (Compound 29);

2-[{1-(4-fluorophenyl)-5-isobutyl-1H-pyrazol-3-yl}methyl]-2,3-dihydro[d]isothiazole 1,1-dioxide (Compound 30);

2-[{1-(2,6-dichlorophenyl)-5-isobutyl-1H-pyrazol-3-yl}methyl]-2,3-dihydro[d]isothiazole 1,1-dioxide (Compound 31);

2-[{1-(tert-butyl)-5-phenyl-1H-pyrazol-3-yl}methyl]-2,3-dihydro[d]isothiazole 1,1-dioxide (Compound 32);

2-[{1-(tert-butyl)-5-(4-fluorophenyl)-1H-pyrazol-3-yl}methyl]-2,3-dihydro[d]isothiazole 1,1-dioxide (Compound 33);

2-[{1-(tert-butyl)-5-(4-trifluoromethylphenyl)-1H-pyrazol-3-yl}methyl]-2,3-dihydro[d]isothiazole 1,1-dioxide (Compound 34);

2-[{1-(tert-butyl)-5-(4-piperidin-1-yl-phenyl)-1H-pyrazol-3-yl}methyl]-2,3-dihydro[d]isothiazole 1,1-dioxide ((Compound 35);

2-[{1-(tert-butyl)-5-(4-cyclohexylphenyl)-1H-pyrazol-3-yl}methyl]-2,3-dihydro[d]isothiazole 1,1-dioxide (Compound 36);

2-{(1-isobutyl-5-phenyl-1H-pyrazol-3-yl)methyl}-2,3-dihydro[d]isothiazole 1,1-dioxide (Compound 37);

2-[{5-(4-fluorophenyl)-1-isobutyl-1H-pyrazol-3-yl}methyl]-2,3-dihydro[d]isothiazole 1,1-dioxide (Compound 38); and a pharmaceutically acceptable salt thereof.

5. A pharmaceutical composition of the compound of claim 1 as an active ingredient.

6. A pharmaceutical composition of the compound of claim 2 as an active ingredient.

7. A pharmaceutical composition of the compound of claim 3 as an active ingredient.

8. A pharmaceutical composition of the compound of claim 4 as an active ingredient.

9. The pharmaceutical composition of claim 5 for treating a pain-related disease is selected from the group consisting of chronic and acute pain, and neuropathic pain; or a high blood pressure.

10. The pharmaceutical composition of claim 6 for treating a pain-related disease is selected from the group consisting of chronic and acute pain, and neuropathic pain; or a high blood pressure.

11. The pharmaceutical composition of claim 7 for treating a pain-related disease is selected from the group consisting of chronic, acute pain, and neuropathic pain; or a high blood pressure.

12. The pharmaceutical composition of claim 8 for treating a pain-related disease is selected from the group consisting of chronic acute pain, and neuropathic pain; or a high blood pressure.

* * * * *